(12) United States Patent
List et al.

(10) Patent No.: US 9,097,679 B2
(45) Date of Patent: Aug. 4, 2015

(54) ANALYTICAL AID

(71) Applicant: Roche Diagnostics Operations, Inc., Indianapolis, IN (US)

(72) Inventors: Hans List, Hesseneck-Kailbach (DE); Karl-Heinz Scherer, Biblis (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 113 days.

(21) Appl. No.: 14/052,269

(22) Filed: Oct. 11, 2013

(65) Prior Publication Data
US 2014/0044608 A1 Feb. 13, 2014

Related U.S. Application Data

(63) Continuation of application No. PCT/EP2012/056493, filed on Apr. 11, 2012.

(30) Foreign Application Priority Data

Apr. 12, 2011 (EP) .................................... 11162068

(51) Int. Cl.
*G01N 21/75* (2006.01)
*G01N 21/78* (2006.01)
(Continued)

(52) U.S. Cl.
CPC .............. *G01N 21/78* (2013.01); *A61B 5/1455* (2013.01); *B05D 5/00* (2013.01); *A61B 2562/0295* (2013.01); *A61B 2562/12* (2013.01); (Continued)

(58) Field of Classification Search
CPC ............... B01L 2300/0816; B01L 2300/0636; B01L 2300/0825; B01L 2200/16; B01L 2300/044; B01L 9/52; G01N 2021/7793; G01N 33/50; G01N 33/54366; G01N 33/54386; G01N 35/00069; G01N 15/0205; G01N 21/01; G01N 2201/0256; G01N 21/8483; G01N 2035/00108; G01N 2035/00148; G01N 21/0303; G01N 21/05; G01N 27/3272; G01N 33/521; Y10S 435/808; Y10S 435/97; B29C 47/0021
See application file for complete search history.

(56) References Cited

U.S. PATENT DOCUMENTS

| | | |
|---|---|---|
| 5,070,886 A | 12/1991 | Mitchen et al. |
| 6,497,845 B1 | 12/2002 | Sacherer |

(Continued)

FOREIGN PATENT DOCUMENTS

| | | |
|---|---|---|
| EP | 1543935 A2 | 6/2005 |
| EP | 2226007 A1 | 9/2010 |

(Continued)

OTHER PUBLICATIONS

Hoenes, J., Mueller, P., Surridge, N., "The Technology Behind Glucose Meters: Test Strips", Diabetes Technology & Therapeutics, vol. 10, Supplement 1, 2008, pp. S-10-S-27.

(Continued)

*Primary Examiner* — Dennis M White
(74) *Attorney, Agent, or Firm* — Roche Diabetes Care, Inc.

(57) ABSTRACT

A process for producing an analytical aid for the detection of at least one analyte in a sample, such as a body fluid. The analytical aid includes at least one housing and at least one test element including at least one test chemistry. The process includes the following steps: providing the test element; and producing at least one housing part of the housing at least one shaping process, during which the test element is connected to the housing part.

26 Claims, 7 Drawing Sheets

(51) Int. Cl.
*A61B 5/1455* (2006.01)
*B05D 5/00* (2006.01)
*G01N 21/01* (2006.01)
*G01N 33/50* (2006.01)
*G01N 15/02* (2006.01)
*G01N 21/77* (2006.01)
*G01N 33/52* (2006.01)
*B29C 47/00* (2006.01)
*G01N 21/03* (2006.01)
*G01N 21/84* (2006.01)
*G01N 33/543* (2006.01)
*G01N 35/00* (2006.01)
*G01N 21/05* (2006.01)
*G01N 27/327* (2006.01)
*B01L 9/00* (2006.01)

(52) U.S. Cl.
CPC ............... *B01L 9/52* (2013.01); *B01L 2200/16* (2013.01); *B01L 2300/044* (2013.01); *B01L 2300/0636* (2013.01); *B01L 2300/0816* (2013.01); *B01L 2300/0825* (2013.01); *B29C 47/0021* (2013.01); *G01N 15/0205* (2013.01); *G01N 21/01* (2013.01); *G01N 21/0303* (2013.01); *G01N 21/05* (2013.01); *G01N 21/8483* (2013.01); *G01N 27/3272* (2013.01); *G01N 33/50* (2013.01); *G01N 33/521* (2013.01); *G01N 33/54366* (2013.01); *G01N 33/54386* (2013.01); *G01N 35/00069* (2013.01); *G01N 2021/7793* (2013.01); *G01N 2035/00108* (2013.01); *G01N 2035/00148* (2013.01); *G01N 2201/0256* (2013.01); *Y10S 435/808* (2013.01); *Y10S 435/97* (2013.01)

(56) References Cited

U.S. PATENT DOCUMENTS

| | | | |
|---|---|---|---|
| 7,553,615 | B2 | 6/2009 | Heindl et al. |
| 2004/0193202 | A1 | 9/2004 | Allen |
| 2005/0214891 | A1 | 9/2005 | Horn et al. |
| 2005/0283094 | A1 | 12/2005 | Thym et al. |
| 2008/0249435 | A1 | 10/2008 | Haar et al. |

FOREIGN PATENT DOCUMENTS

| | | |
|---|---|---|
| WO | 0136010 A1 | 5/2001 |
| WO | 03009759 A1 | 2/2003 |
| WO | 2007012494 A1 | 2/2007 |
| WO | 2010094426 A1 | 8/2010 |
| WO | 2010094427 A3 | 8/2010 |

OTHER PUBLICATIONS

Banauch, V., Bruemmer,W., Ebeling, W., Metz, H., Rindfrey H., Lang, H., "A glucose dehydrogenase for glucose determination in body fluids", Z. Klin. Chem. Klin. Biochem., 13th year 1975, pp. 101-107.

Bergmeyer, H.U., "Methods of Enzymatic Analysis", 2nd edition, vol. 1, Verlag Chemie Weinheim/Bergstr. 1970, pp. 417-419.

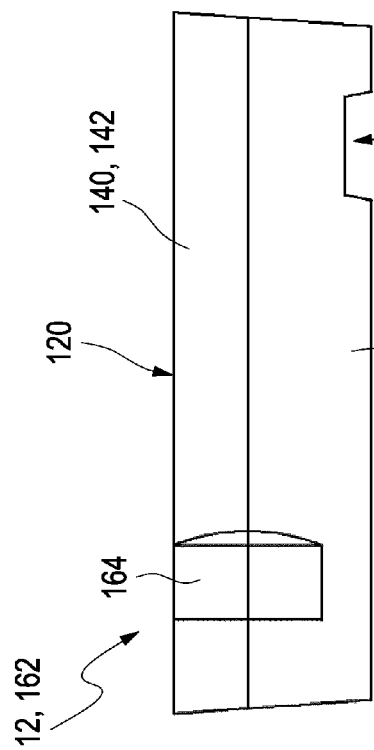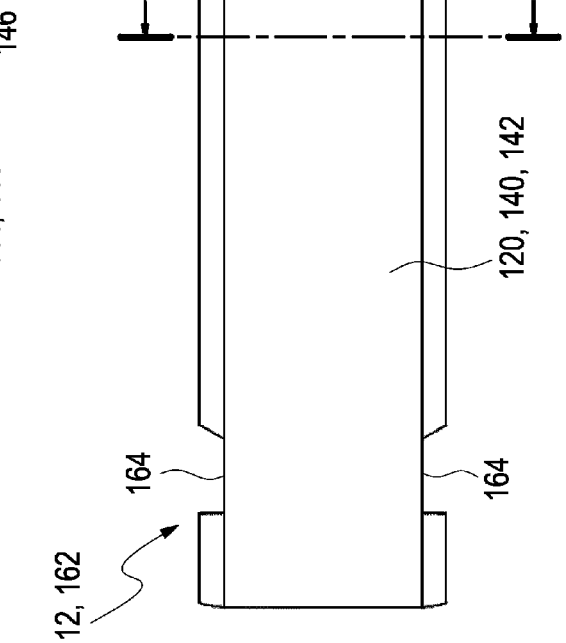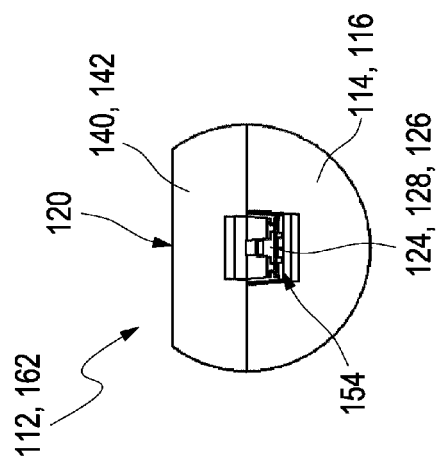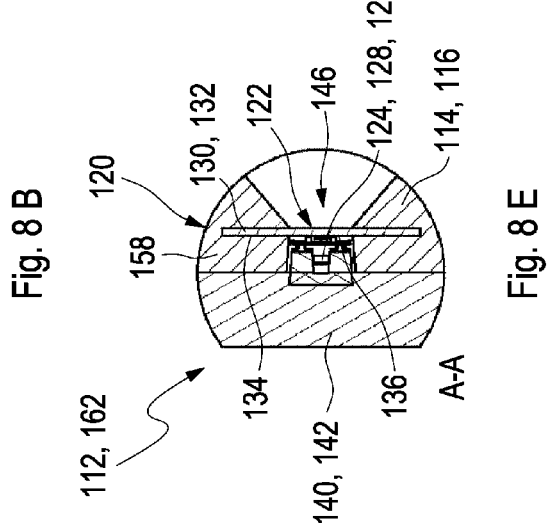

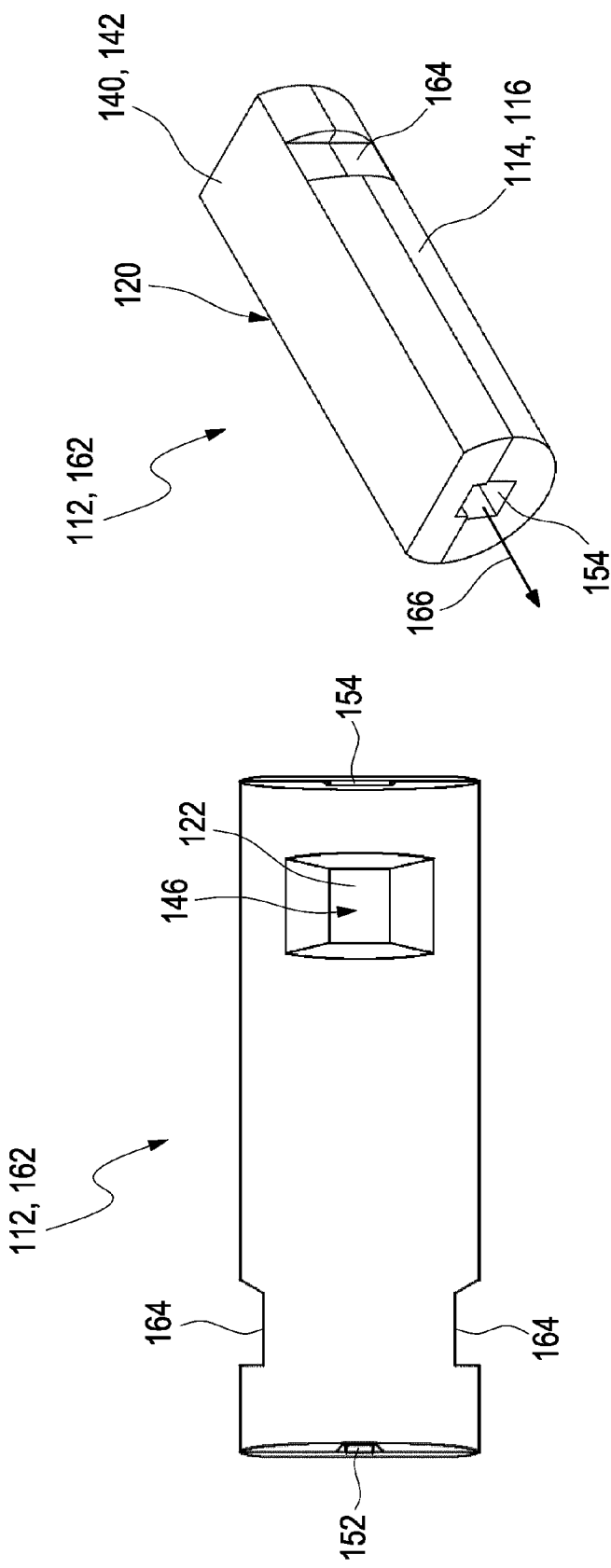

ANALYTICAL AID

CROSS-REFERENCES TO RELATED APPLICATION(S)

This application is a continuation of and claims priority to International Patent Application no. PCT/EP2012/056493 which was filed on Apr. 11, 2012 which in turn claims priority to European patent application no. 11 162 068.8 filed on Apr. 12, 2011.

FIELD OF THE INVENTION

The invention relates to an analytical aid for the detection of at least one analyte in a sample and to a process for producing such an analytical aid. In addition, the invention relates to an analytical magazine comprising a plurality of such analytical aids. Such analytical aids are generally used especially in medical diagnostics for the qualitative or quantitative detection of one or more analytes in samples, more particularly liquid samples and particularly preferably body fluids, such as blood, interstitial fluid, saliva or urine. For example, these analytes can be one or more metabolites, for example blood glucose.

DESCRIPTION OF THE RELATED ART

In the field of diagnostics, it is necessary in many cases to obtain samples of body fluid, more particularly blood samples or samples of interstitial fluid, so that one or more analytes therein can be detected, especially in a specific manner. Examples of such analytes, which can also be detected in the context of the present invention, are glucose, more particularly blood glucose, coagulation parameters, triglycerides, lactate, cholesterol or combinations of the aforementioned analytes and/or other metabolites. Depending on the concentrations detected, it is then possible, for example, to make a decision about appropriate treatment.

For the purpose of analyte detection, one or more analytical aids are generally used in order to obtain and/or to analyze the samples. Thus, the analytical aids can comprise, for example, one or more lancets, i.e. elements which are designed to generate in a user's skin an opening through which the body fluid can be withdrawn. With regard to examples of such lancets, reference can be made to WO 01/36010 A1. Alternatively or in addition, the analytical aids can comprise one or more test elements comprising one or more test chemistries which can be designed to change certain detectable properties upon exposure to the analyte to be detected. For example, analyte detection can comprise detection of electrochemical properties of the analytes themselves and/or of other substances, and/or a change in electrochemically detectable properties. Alternatively or in addition, it is also possible, for example, to detect optical properties and/or changes therein. For a description of possible test chemistries, reference can be made to, for example, J. Hones et al.: Diabetes Technology and Therapeutics, vol. 10, Supplement 1, 2008, S-10 to S-26. In addition, reference can be made to, for example, WO 2010/094426 A1 or WO 2010/094427 A1. These documents also describe analytical aids comprising a test chemistry which is also usable in principle in the context of the present invention.

EP 1 543 934 A2 discloses an injection-molded plastics part having an embedded component, and a corresponding production process. This document describes, for example, the production of what are known as analytical chips which are overmolded with a plastic frame. Paragraph [0028], inter alia, describes a process in which a glass body is surrounded by a plastic frame. More particularly, the process is suitable for the production of what are known as biochips. In the case of these biochips, the untreated surfaces of the glass support are coated at a later stage, i.e. after the connection of the plastic frame to the glass support, with appropriate reagents required for usage of biochips.

In addition, integrated analytical aids are known which are used not only for the purpose of generating the sample of body fluid, but also for the purpose of transportation of the sample and, optionally, even for the purpose of qualitative and/or quantitative analysis of said sample.

Examples of such analytical aids are aids containing what are known as microsamplers, in which a lancet is used to make a prick or a cut and in which the sample is accommodated and is transported to one or more test fields comprising the test chemistry. These test fields can be arranged separately from the lancet, but can also be a component of the lancet itself. Such systems, which are described in, for example, US 2004/0193202 A1, US 2008/0249435 A1, WO 03/009759 A1, WO 2010/094427 A1 or WO 2010/094426 A1, are especially user-friendly owing to their high degree of integration.

EP 2 226 007 A1 describes an analytical magazine comprising chambers in which analytical aids are stored. The analytical aid comprises at least one test element for the detection of at least one analyte in a sample of a body fluid. The test element comprises a test field, with the test field being at least partly arranged within the respective chamber and with a wall of the chamber at least partly covering the test field and at least partly delimiting a test field area accessible from the chamber. For example, paragraph [0055] explains that the test field can also be connected to the housing in a time-independent and/or process-independent manner with respect to the connection of a membrane to the housing. The test fields can be applied at a later time, and so half-finished elements can be temporarily stored without test fields.

US 2005/0283094 A1 describes a test device for testing a body fluid, the test device comprising a test strip, a piercing element and a housing. As described in paragraph [0052] for example, the test strip and the housing can also be in the form of a single body, and so the housing or a part thereof also functions as a test strip. For example, a shaping process can be used to produce said single-body test element housing.

Analytical aids are generally provided or produced in the form of magazines in which a plurality of such analytical aids is accommodated. For example, these analytical aids, which are generally in the form of disposables, are inserted into a one-piece or multi-part magazine body during production. However, this insertion procedure is in practice comparatively complex, since generally very small structures have to be fitted with very small disposables. Particularly in the case of analytical aids in the form of test elements which are firmly integrated into a magazine, this procedure is complex since partial adhesiveness of the magazine has to be produced first, for example by printing adhesive in a targeted manner or by inserting a piece of double-sided adhesive tape. Only thereafter is it generally possible to mount an actual test field comprising the test chemistry.

OBJECT OF THE INVENTION

It is therefore an object of the present invention to provide an analytical aid and a process for producing an analytical aid which at least substantially avoid the disadvantages of known analytical aids and processes. More particularly, the process shall be realizable in a cost-effective manner and implementable on an industrial scale, and more particularly the complexity of integrating the test chemistry into the analytical aid shall be reduced compared to known production processes.

SUMMARY OF THE INVENTION

This object is achieved by the invention having the features of the independent claims. Advantageous developments of the invention, which are realizable alone or in any combination, are presented in the dependent claims.

In a first aspect of the present invention, a process for producing an analytical aid for the detection of at least one analyte in a sample is proposed. As explained above, in the context of the present invention, an analytical aid is generally understood to mean a device which is designed to qualitatively or, preferably, quantitatively detect at least one analyte, especially in a specific manner, and/or which can be used for such analyte detection, for example for obtaining the sample and/or for detecting the analyte in the sample. Said at least one analyte can in principle be any desired detectable substance. Particularly preferably, said analyte is at least one metabolite, more particularly one or more of the metabolites mentioned at the beginning. The sample can in particular be a body fluid, for example, as explained above, blood, interstitial fluid, saliva or urine. The analytical aid can be designed to carry out detection of the analyte independently, providing for example the result of the detection immediately, or in combination with a test instrument or a test device which uses the analytical aid. The analytical aid can in particular be in the form of a disposable, i.e. usable for just one test. As will be explained in more detail below, the analytical aid can in particular be a component of an analytical magazine or be accommodated in an analytical magazine, the analytical magazine comprising a plurality of analytical aids which are preferably connected to one another, for example rigidly connected to one another and/or in the form of a single body. For example, it is possible to realize an analytical magazine having a magazine housing, with the analytical magazine comprising a plurality of analytical aids which, for example, are accommodated in the magazine housing and/or which are connected to one another via the magazine housing. For example, the housings of the analytical aids or parts thereof can be, entirely or partly, components of the magazine housing. Alternatively, it is, however, also possible to realize individual analytical aids. Thus, the invention can also relate to individual analytical aids which, for example, are designed for exactly one use.

Thus, the analytical aid according to the present invention can be in particular an individual test. An individual test is understood to mean here an individual analytical aid which can be handled individually, independently of other analytical aids and without direct mechanical connection to other analytical aids. Alternatively, a plurality of analytical aids can also be accommodated in a single magazine or even be combined to form a single magazine, for example by said analytical aids being mechanically connected to one another, for example by means of a common housing.

The analytical aid comprises at least one housing and at least one test element comprising at least one test chemistry. A housing is generally understood to mean an element which can be in the form of one piece or multiple parts and which is designed to at least substantially seal off the analytical aid from the outside and/or to provide mechanical protection for the analytical aid, more particularly mechanical protection with respect to external influences. Accordingly, the housing can typically be rigid so that it does not deform or is only negligibly deformed under the influence of, for example, usual mechanical forces which occur during use, more particularly under the influence of its own weight. For example, the housing can have a housing wall which has, in at least one region, a wall thickness of at least 0.5 mm, preferably at least 1.0 mm. However, alternatively or in addition, deformable housings are also usable in principle. As will be explained in more detail below, the housing can in particular have an interior space which is completely or partly enclosed by the housing or parts of the housing, for example at least one chamber. Said chamber can have, for example, one or more openings through which, for example, intrusion of one or more actuators into the chamber is possible and/or through which transfer of the sample into the chamber is possible and/or through which at least one change in property of the test element and/or of the test chemistry can be detected.

Particular preference is given to an embodiment in which the analytical aid has at least one chamber, i.e. at least one interior space or cavity which is completely or partly enclosed by the housing. For example, the chamber can have an interior space which is enclosed by the housing and which can only be accessed via one or more openings. Preferably, the analytical aid is configured such that at least one test field area faces the chamber, and so, from the chamber, the test field area of the test element is accessible for sample input onto the test field area.

As also explained below, the analytical aid can particularly preferably also comprise at least one lancet element. Said lancet element can in particular be completely or partly accommodated in the at least one chamber, preferably movably. Thus, the analytical aid can, for example, comprise exactly one chamber, with exactly one lancet element which is stored in the chamber, preferably movably, and so it is for example possible to carry out, via an opening in the housing, a piercing movement in which a lancet tip of the lancet element emerges from the opening. Preferably, the lancet element can be remagazined in the chamber after the piercing movement. In addition, the test element can, for example, comprise at least one test field area facing the chamber.

Alternatively, it is also possible, for example, to provide a plurality of analytical aids, each comprising one or more chambers, it being possible, for example, to combine said plurality of analytical aids to form the analytical magazine. For example, the analytical magazine and/or the analytical aids can comprise a plurality of chambers, each chamber preferably accommodating exactly one lancet element, preferably movably, and so it is for example possible to carry out, via an opening in the housing, a piercing movement in which a lancet tip of the lancet element emerges from the opening. In this case, too, each chamber is preferably provided with at least one test field area of the at least one test element, the test field area facing the chamber and it being possible to apply sample to the test field area from the chamber. For example, in the analytical magazine, it is possible for a chamber with the associated lancet element, optionally the at least one test field area associated with the chamber, and the housing enclosing the chamber to form in each case an analytical aid, with a plurality of similar or different analytical aids being combined to form the analytical magazine.

In the context of the present invention, a test chemistry is to be understood to mean a substance which can comprise one or more chemical components which are designed to change at least one detectable property in the presence of the analyte. For example, said at least one detectable property can be at least one electrochemical property and/or at least one optical property. With regard to possible embodiments of test chemistries, reference can be made to, for example, the above description of the prior art. The invention will be described below substantially with reference to test chemistries which change at least one optically detectable property, for example a color, in the presence of the at least one analyte. Accordingly, the test chemistry can, for example, be designed to implement a color change in the presence of the analyte. However, alternatively or in addition, other types of test chemistry are also usable in principle, for example electrochemical test chemistries.

In the context of the present invention, a test element is understood to mean a one-piece or multi-part, preferably one-piece, element which comprises the at least one test chemistry. As will be explained in more detail below, the test element can, for example, comprise at least one support element into which the test chemistry is introduced and/or onto which the test chemistry is applied. More particularly, the at least one support element can be produced and/or provided separately from the housing. For example, the at least one support element can comprise at least one plastic material, but, alternatively or additionally, other materials are also usable in principle, for example ceramic materials and/or paper materials and/or glass materials. Composite materials are also usable in principle. A support element is generally understood to mean an element which is designed to support the test chemistry, for example by the test chemistry being applied to the support element in the form of one or more layers. However, alternatively or additionally, the support element can also, for example, serve as matrix material or comprise a matrix material into which the test chemistry is introduced. On the other hand, alternatively or additionally, the support element can also comprise one or more recesses, for example one or more indentations, into which the test chemistry can be introduced. Various embodiments are possible.

In contrast to the above-mentioned prior art, more particularly EP 1 543 934 A2, in the process proposed according to the invention, the test element comprising the test chemistry is connected to the housing part in the shaping process. More particularly, this can take place such that the support element comprising the test chemistry applied thereto is introduced into the shaping process and is connected there to the housing part, for example by introducing the test element with the support element and the test chemistry applied thereto into a mold of the shaping process and contacting it there with at least one housing material of the housing part. In this process, the support element and/or the test chemistry can be contacted with the housing material of the housing part. For example, the support element with the test chemistry applied thereto can be completely or partly subjected to in-mold coating with the housing material and/or be partly embedded in the housing material. This achieves a considerable simplification of the process. In contrast to this, in EP 1 543 934 A2 for example, one surface of the glass support is coated with appropriate reagents at a later stage, i.e. after the connection of the glass support to the plastic frame. However, such a step requires elaborate cleaning of the glass surface. In addition, especially in the case of small-volume analytical aids, such a subsequent coating with test chemistry is barely possible, since the areas to be coated are generally inaccessible or difficult to access and are generally so small that a very elaborate and highly precise application of the test chemistry would be required. This considerable complexity of the prior art can be avoided by the process proposed according to the invention.

At the same time, the test element can be produced separately and subjected only afterwards to the shaping process. Thus, the proposed process differs from, for example, the process described in EP 2 226 007 A1, in which the actual test element is produced only during the shaping process. Compared with this, the process according to the invention provides the advantage that, for example, a support element of the test element does not have to be optimized at the same time with respect to its mechanical properties for use as housing material. The test element can be produced and optimized separately with respect to its manufacture and/or with respect to its components.

It is particularly preferred for the support element, entirely or partly, to be in the form of a film element or to comprise such a film element. A film element is to be understood to mean an element whose lateral extent exceeds its thickness by at least a factor of 10, preferably by at least a factor of 100 and particularly preferably by at least a factor of 1000. For example, the film element can deform, under the influence of its own weight, perpendicular to its lateral extent. The film element can in particular be in the form of a flat film element having a thickness of less than 1 mm, preferably having a thickness of not more than 500 micrometers. For example, the film element can have a thickness of from 50 micrometers to 1 mm, more particularly a thickness of from 100 micrometers to 500 micrometers and particularly preferably a thickness of from 140 micrometers to 250 micrometers. The film element can in particular be flexible or deformable. It is particularly preferred for the film element to have an annular shape, for example to be in the form of a circular ring.

The support element can in particular be, entirely or partly, in the form of an optically transparent support element. An optically transparent support element is generally to be understood to mean an element which exhibits a transparency for optical signals in the ultraviolet and/or visible and/or infrared spectral range. For example, it is possible to have a transparency for at least one wavelength in a wavelength range between 200 nm and 400 nm and/or a transparency for at least one wavelength in a wavelength range between 400 nm and 800 nm and/or a transparency for at least one wavelength in a wavelength range between 800 nm and 1600 nm. Transparency is to be understood to mean a property in which signals of the wavelengths mentioned, after passing through the support element, for example after passing through perpendicular to one surface of the film element, exhibit an intensity which has at least 10%, preferably at least 30% and particularly preferably at least 60% of the intensity prior to passage through the support element.

The proposed process for producing the analytical aid comprises the steps described below. These steps can typically be carried out in the order presented. In addition, it is, however, also possible for individual steps or a plurality of these steps to be carried out in a different order, overlapping in time or at the same time. In addition, individual steps or a plurality of these steps can be carried out repeatedly. In addition, additional process steps not presented below can be carried out.

The process steps are:
a) providing the test element; and
b) producing at least one housing part of the housing by means of at least one shaping process, during which the test element is connected to the housing part.

Providing the test element can, for example, be understood to mean production of the test element. However, alternatively or additionally, providing the test element can also generally involve any desired manner of introducing the test element into the process such that the test element is integrated into the analytical aid. For example, analytical aids can also be produced and provided by another manufacturer and/or in a separate manufacturing plant and/or be produced in an independent production plant. The test element can be provided alone, or a plurality of test elements can also be provided at the same time, for example all the test elements for all the analytical aids of an analytical magazine and/or a test element for a plurality of analytical aids. Providing the test element can be carried out in an individual process or else in a continuous or batchwise provision process for a plurality of analytical aids, for example in the form of a tape product, a tape comprising for example a plurality of test elements which can be provided successively at one application site.

In the context of the present invention, a housing part of the housing is to be understood to mean a component of the housing which, alone or after combination with one or more further housing parts, forms the housing according to the above definition. More particularly, it is possible to form the housing from a plurality of housing parts in the form of housing parts connected to one another with a force fit and/or cohesively and/or with a form fit, for example in the form of a housing base as first housing part and in the form of a housing cover as second housing part and/or in the form of an upper shell as first housing part and in the form of a lower shell as second housing part.

In the context of the present invention, a shaping process is understood to mean a process in which at least one housing material and/or at least one starting material which produces at least one housing material is shaped such that the housing part is produced. For example, said housing material and/or said at least one starting material can comprise at least one plastic material and/or at least one starting material for a plastic material. In the latter case, it is possible to use, for example, at least one polymerizable and/or crosslinkable and/or curable starting material or a combination of a plurality of such starting materials. For example, it is possible to use one or more reaction resins and/or one or more light-curing and/or thermally curable resins, for example one or more epoxy resins. Alternatively or in addition, as will be explained in more detail below, it is also possible to use, for example, one or more thermoplastics and/or one or more thermoset plastics and/or one or more elastomeric plastics.

For example, the shaping process can comprise at least one casting process. Said casting process can, for example, comprise a process in which one or more resins, more particularly casting resins, are introduced into the mold cavity. However, alternatively or in addition, the casting process can also comprise at least one thermal casting process, more particularly an injection-molding process.

For example, the shaping process can comprise at least one casting process, more particularly a casting process in which at least one housing material and/or at least one starting material for a housing material are introduced into at least one mold cavity by means of a casting process. A casting process is generally to be understood to mean a process in which at least one housing material and/or at least one starting material for a housing material in liquid, viscous or deformable form, this optionally also including the possibility of using at least one housing material having thixotropic properties and/or at least one thixotropic starting material for a housing material, is introduced into at least one mold cavity. For example, the housing material can be introduced as a melt into the mold cavity. The casting process can be carried out under negative pressure, under normal pressure or else under positive pressure.

For example, the casting process can also comprise at least one injection process, more particularly a thermal injection process, for example an injection-molding process. In the context of the present invention, an injection-molding process is generally to be understood to mean a process in which at least one melt of at least one housing material is introduced into at least one mold cavity, for example at least one plastics melt. For example, use can be made of an injection-molding machine in which the at least one housing material is plasticized in at least one injection unit and is subsequently injected into at least one mold cavity of at least one injection-mold.

The housing material and/or the starting material can, for example, be introduced into the mold cavity of the mold under a pressure of at least 2 bar, preferably at least 10 bar, more particularly even at least 100 bar, at least 500 bar or even at least 1000 bar.

As will be explained in more detail below, the shaping process can comprise in particular at least one plastics shaping process and preferably a thermoforming process, i.e. a process in which the housing material is shaped at an elevated temperature, for example a temperature of at least 50° C., more particularly at least 60° C., preferably at least 80° C. and particularly preferably at least 100° C. This can, for example, be carried out in the context of an injection-molding process. The shaping process can, for example, be carried out using at least one shaping mold, for example using a mold which comprises at least one mold cavity in which the housing part is fully or partly shaped. The shaping process can in particular be configured such that, after the shaping process has been carried out, the housing part already assumes its final shape, i.e. more particularly the shape which the housing part assumes later in the housing of the analytical aid. The plastics shaping process can in particular be selected from the group consisting of in-mold coating and overmolding. However, alternatively or in addition, other plastics shaping processes are also usable.

As explained above, during the housing part shaping process, the test element is connected to the housing part. This means that the connection of the test element is carried out at the same time as the shaping process and/or is carried out overlapping in time with the shaping process. More particularly, the test element can be connected to the housing part by the shaping process, i.e. by means of and/or owing to the shaping process, and so the procedure for connecting the test element to the housing part and the procedure for the shaping process are at least partly identical.

Connection of the test element to the housing part can in principle be understood to mean any desired procedure in which, after it has been carried out, the test element and/or at least part of the test element is connected to the housing part with a force fit and/or a form fit and/or cohesively, and so the test element is preferably no longer movable relative to the housing part or, for example, only with a tolerance which is preferably not more than 1 mm in any direction, preferably not more than 0.5 mm and particularly preferably not more than 0.2 mm or even not more than 0.1 mm or even without any play. The connection can in particular be a direct connection, i.e. a connection without an indirect connecting element, for example an adhesive. Thus, during the shaping process, the test element can in particular be connected directly to the housing part without using one or more indirect connecting elements such as adhesives for example.

More particularly, the test element can be connected to the housing part such that at least one region of the test element, for example at least one surface area, contacts the housing part. The process can in particular be carried out such that, during the shaping process, the test element is connected to the housing part such that the test element rests on the housing part at at least one surface area. This surface area can also be referred to as a connection surface area. Resting of said test element should be carried out directly, i.e. without interposition of one or more connecting elements such as adhesives for example. Resting of the test element can, for example, be carried out on just one side of the test element. For example, during the shaping process, the test element can be connected to the housing part such that said test element rests on the housing part via a first side, for example via a first surface of a film element, and it is possible, for example, for a second surface, for example an opposite surface of the film element, not to be resting. However, alternatively or in addition, the process can also be carried out such that, during the shaping process, the test element is at least partly embedded in the housing part. This means that the test element or parts thereof, for example one or more parts of the support element, are completely or partly enclosed in at least two dimensions, preferably in at least three dimensions, by at least one housing material of the housing part, for example such that there is direct contact between the housing material and the test element.

As explained above, the test element can in particular be connected to the housing part in a manner selected from the group consisting of a cohesive bond, a form-fit connection and a force-fit connection. Combinations of the aforementioned connection types are also possible. Particular preference is given to a form-fit connection and/or a force-fit connection, more particularly in a direct manner, and so there is direct contact between the test element and the housing part.

If the housing comprises a plurality of housing parts, the above-described process step b) relates to at least one of these housing parts, and so, for example, the housing can also comprise one or more housing parts to which the test element is not connected. The process can be carried out using one or more test elements.

As described above, the shaping process can in particular comprise at least one plastics shaping process. A plastics shaping process is understood to mean a process in which at least one housing material in the form of at least one plastic and/or at least one raw material of a plastic is subjected to a shaping process. The plastic can in particular be a thermoplastic, for example a thermoplastic which is already present chemically in its final form prior to the shaping process and which is merely reshaped in terms of its outer shape by the shaping process. However, other plastics are also usable. For example, use can be made of one or more raw materials of a plastic which only form a plastic during the shaping process, for example by means of a chemical reaction, more particularly polymerization and/or crosslinking.

More particularly, the plastics shaping process can be at least one thermoforming process or comprise at least one thermoforming process. As explained above, a thermoforming process is to be understood to mean a shaping process in which heat input into at least one housing material is carried out. This can, for example, be carried out using at least one heated mold, for example using at least one heated mold having at least one mold cavity. The plastics shaping process can in particular be selected from the group consisting of: a casting process, more particularly an injection-molding process; a compression process, more particularly a transfer-molding process. However, combinations of the aforementioned processes and/or use of one or more other plastics shaping processes are also possible in principle.

It is particularly preferred for the plastics shaping process to be selected from the group consisting of in-mold coating and overmolding, and combinations of these techniques are also possible. Thus, the process of connecting the test element to the housing part can in particular comprise in-mold coating or overmolding, for example film in-mold coating and/or film overmolding. In the case of in-mold coating and overmolding, the test element is first at least partly inserted into a mold, for example into the mold cavity of a mold, and so part of the mold cavity remains free. This part is subsequently filled, for example, with one or more plastics materials and/or with one or more raw materials of a plastics material, for example in the form of a casting process, an injection process or a compression process. In the case of in-mold coating, the insertion of the test element into the mold cavity is carried out such that one side of the test element comes into direct contact with the plastics material. In the case of overmolding, the insertion is carried out such that the test element is at least partly enclosed in at least two dimensions, more particularly in three dimensions, by the plastics material.

Thus, it is possible in general in the above-described process step b) to insert at least part of the test element into a shaping mold and to at least partly contact it, in the shaping mold, with a housing material of the housing part, for example a plastics material. Said contacting can be carried out on one side.

In the case of a film element, said contacting can, for example, be carried out on one film side. However, alternatively or in addition, contacting can also be carried out in two or more dimensions, and so the test element is, for example, at least partly enclosed in two or three dimensions by the housing material during envelopment. In both cases, there should preferably be direct contact between the housing material and the test element or parts thereof.

If a shaping mold is used, it is particularly preferred for the at least one test element part inserted into the shaping mold to rest, via at least one section, on at least one wall of the shaping mold. In this way, it is possible, for example, to ensure that said section resting on the wall of the shaping mold is not covered by the housing material. Alternatively or in addition, said section resting on the wall of the shaping mold can, for example, be temperature-adjusted separately.

For example, process step b) can be carried out such that the wall of the shaping mold, at least in the region on which the section of the test element rests on the wall, has a temperature of not more than 130° C., preferably not more than 120° C. and particularly preferably not more than 110° C. while process step b) is being carried out. This can, for example, be effected by appropriate temperature adjustment of the mold. For example, this upper temperature limit can be present when using a casting process, more particularly an injection-molding process. In addition, particularly when using a thermal shaping process and, particularly preferably, an injection-molding process, process step b) can, for example, be carried out such that the wall of the shaping mold, at least in the region on which the section of the test element rests on the wall, has a temperature of at least 25° C. while process step b) is being carried out, more particularly at least 30° C., preferably at least 40° C. and particularly preferably at least 50° C., for example by appropriate temperature adjustment of the shaping mold. For example, process step b) can be carried out such that, particularly when using a thermal shaping process and, particularly preferably, an injection-molding process, the wall of the shaping mold, at least in the region on which the section of the test element rests on the wall, has a temperature of from 30° C. to 130° C. while process step b) is being carried out, more particularly from 40° C. to 120° C. and particularly preferably from 50° C. to 110° C., for example by appropriate temperature adjustment of the shaping mold. Such temperature adjustments can, for example, be determined by what are known as FEM simulations, which are routinely carried out in many cases during mold design, and/or by other simulations and/or empirical methods. Thus, by means of appropriate mold design and/or by suitable operation of the mold, it is possible to ensure that the above-mentioned temperatures are maintained.

The at least one section of the test element which rests on the wall can, for example, be one side of a strip-shaped and/or disc-shaped test element. More particularly, the section of the test element which rests on the wall can comprise at least part of the test chemistry, more particularly a test field area of the test chemistry. Thus, it is possible, for example, to ensure that the test chemistry is not covered or at least not completely covered by the housing material. In addition, it is possible to ensure that the test chemistry, during the shaping process, is only exposed to a temperature at which said test chemistry, at least for a short time, does not suffer any damage.

The analytical aid can in particular comprise at least one chamber, i.e. a cavity, which is completely or partly surrounded and/or delimited by the housing material of the housing. The test element can in particular comprise a test field area in which the test chemistry faces the interior space of the chamber and is thus preferably accessible from the chamber for sample input. Even complex structures of this kind having test field areas arranged inside a chamber are easily realizable by the process according to the invention, since, in contrast to the prior art, subsequent coating of the test field areas with test chemistry after the production of the housing is not required. Such a structure would not be realizable by, for example, the process described in EP 1 543 934 A2.

The shaping process can in general be carried out especially free of release agent. This means that, preferably on one wall of the mold cavity which comes into contact with the housing material and/or the test element, preferably no release agent is applied, and so the housing material and/or the test element preferably rest directly on the wall of the mold cavity of the shaping mold.

In addition, the process can in particular be carried out such that, in process step b), the test element is connected to the housing part such that at least one surface of the test chemistry as test field area for input of the sample remains uncovered by a housing material of the housing part. Thus, a test field area is to be understood to mean a surface of the test chemistry which can be used for detection of the analyte and which can come into contact with the sample or a constituent of the sample, for example by applying the sample to the test field area perpendicular to the test field area or parallel to the test field area. Said application can, for example, be effected by means of a transfer element and/or directly.

This uncovered configuration of the test field area, it also being possible to provide a plurality of test field areas, can be effected in various ways. For example, as described above, the test element can be subjected to in-mold coating such that the test field area is arranged on one side, opposing the housing part, of the support element, and so for example, on a first side, the support element is in contact with the housing part and, on an opposing second side, the test chemistry is applied to the support element. However, other configurations are also possible in principle. Alternatively or in addition, the uncovered configuration of the test field area can also be effected such that although the support element on the side of the test chemistry is partly covered by the housing material or comes into contact with the housing material, the test field area remains uncovered, for example by the housing part on the side of the test field area forming one or more input windows through which the test field area is accessible for sample input, with the input windows, for example, completely or partly framing the test field area. The test field area can be accessible from an outer side of the housing or can, as will be explained in more detail below, be arranged particularly inside a chamber, and so, for example, sample input can be effected from the interior space of the chamber.

In addition, the process can in particular be carried out such that the housing is configured such that at least one observation window is produced in the housing, wherein the test chemistry, more particularly the test field area, can be monitored optically through the observation window, for example from outside. Thus, it is possible in particular to form at least one observation window in the housing, for example one or more observation windows per analytical aid, wherein the test field area can be optically monitored through the observation window. Said monitoring can be carried out directly or indirectly, for example by permitting a direct view of the test field area and/or the test chemistry through the observation window in the housing. However, alternatively or in addition, optical monitoring can also be carried out through one or more optically transparent elements, and with regard to optical transparency, reference can be made to the definition above. For example, this optically transparent element can be a constituent of the housing. However, alternatively or in addition, the optically transparent element can also comprise the optional support element of the test element, and so, for example, the monitoring of the test field area can be achieved through the support element, which can be completely or partly configured as an optically transparent support element. Thus, it is possible, for example, for the observation window to permit, from an outer side of the housing, a view of a back side of a support element of the test element, for example a film back side of the support element, with the test field area being arranged on a front side opposing the back side, and so observation through the support element is possible. As described above, the test field area can, for example, be arranged inside a chamber, and so the test field area inside the chamber is observable through the observation window.

As described above, the test chemistry can in particular be applied to the support element in the form of one or more layers. In addition to the at least one test chemistry, further elements can be arranged on the support element. For example, it is possible to provide a multilayer structure comprising at least one layer of test chemistry and at least one further layer, for example a layer comprising at least one optical pigment and/or at least one separation layer which makes it possible to separate constituents of the sample before the sample reaches the test chemistry. Thus, it is possible, for example, to choose a layered structure in which, firstly, the at least one test chemistry is applied to the support element, followed by at least one separation layer and/or at least one pigment layer, and so upon application of the sample, the sample first has to penetrate the separation layer and/or pigment layer before it reaches the test chemistry. Hereinafter, no distinction is made conceptually between these options, and so the test chemistry can also comprise a multilayer structure, with at least one layer comprising the actual test chemistry and at least one optional further layer being free of test chemistry. In this respect, the test field area is to be understood as a sample input area for input of the sample, and upon input of the sample to this sample input area, the sample or constituents of the sample are able to reach the test chemistry directly or after penetrating one or more test-chemistry-free layers, optionally through one or more separation layers and/or pigment layers. Thus, the test field area can comprise a free surface of test chemistry which is directly accessible for input of the sample, or can, alternatively or in addition, be at least one sample input area of at least one further test-chemistry-covering layer, with it being possible for the sample or at least part of the sample to penetrate the at least one further layer (for example the at least one separation layer and/or pigment layer) in order to reach the test chemistry. The optional at least one separation layer and/or pigment layer can, for example, be used to remove red blood cells from a blood sample and to shield them optically from the observation window, since they might, for example, prevent and/or impede optical monitoring of a color change in the test chemistry. Thus, the separation layer and/or pigment layer can comprise, for example, pigments which permit reflection of excitation light which enters the test chemistry through the observation window and through the support element. The pigments can, for example, be or comprise titanium dioxide particles.

In addition, the process can in particular be carried out such that the housing forms at least one chamber. For example, it is possible to provide per analytical aid exactly one chamber which, as explained above, can also comprise one or more openings. The test field area can in particular face an interior space of the chamber.

If the housing comprises at least one chamber, the process can in particular comprise in addition at least one process step in which at least one lancet element for generating the sample is introduced into the chamber, more particularly at least one microsampler. If a plurality of chambers is provided, for example identical chambers, for example one chamber per analytical aid, it is possible, for example, to introduce in each case exactly one lancet element per chamber. A lancet element is generally to be understood to mean an element which is designed to generate a prick and/or a cut in a user's skin surface. Thus, the lancet element can, for example, comprise a tip and/or a blade and/or a sharp edge which makes it possible to generate the prick and/or cut. A microsampler is to be understood to mean a lancet element which comprises in addition at least one capillary element, for example at least one capillary slit in a surface of the lancet element. For example, a capillary slit can extend from a lancet tip of the lancet element into a lancet body. The capillary element is used for the uptake and/or for the forwarding of the sample or of constituents thereof.

The test chemistry can in particular be selected in terms of stability such that it is stable, at least for a short time, with respect to temperatures of 100° C., more particularly with respect to temperatures of 110° C. and particularly preferably with respect to temperatures of 120° C. For instance, with regard to possible test chemistries, reference can be made in general, for example, to the above-described prior art, for example to the above-cited WO 2010/094426 A1, WO 2010/094427 A1 or to J. Hones et al.: Diabetes Technology and Therapeutics, vol. 10, Supplement 1, 2008, S-10 to S-26. However, as explained above, particular preference is given to a temperature-stable test chemistry, i.e. a test chemistry which is stable, at least for a short time, with respect to temperatures of 100° C., more particularly with respect to temperatures of 110° C. and particularly preferably with respect to temperatures of 120° C. A test chemistry which is stable, at least for a short time, with respect to the aforementioned temperatures is understood to mean a test chemistry which, during an exposure time of at least 1 minute, preferably at least 5 minutes, decreases in terms of its activity at the aforementioned temperatures by preferably less than 50%, more particularly less than 30% and particularly preferably less than 20%. For example, to test these properties, the test chemistry, preferably in the form of dry chemistry on the support element, can be exposed to the aforementioned temperatures for the aforementioned times, for example for 1 minute or 5 minutes. Before or after this temperature exposure, the activity is measured. The activity can in principle be determined by means of any desired method known from the prior art, since in the context of the present definition only the percentage decrease in activity during the temperature exposure is of relevance. The activity can in particular relate to enzymatic activity of the test chemistry, more particularly of a dry chemistry, more particularly in a test strip. For example, methods are known which, for measurement of enzymatic activity, extract the enzyme from the test chemistry or the test element and subsequently determine, for example, the activity by means of ultraviolet absorption. In this regard, reference can be made, for example, to H. U. Bergmeyer: Methoden der enzymatischen Analyse [Methods of enzymatic analysis], Verlag Chemie, 2nd edition 1970, p. 417 or to Banauch et al.: A glucose dehydrogenase for the determination of glucose concentrations in body fluids, Z. Klin. Chem. Klin. Biochem. 1975 March; 13(3): 101-7. For example, for the test of stability and/or of activity decrease, a test element, for example a test strip, comprising the test chemistry can be produced. Subsequently the enzymatic activity of an enzyme of the test chemistry can be measured using a customary method, then the above-described storage at an elevated temperature is carried out, and subsequently the same method for measurement of enzymatic activity is carried out again. The procedure is typically carried out using a representative group of test elements or test chemistries.

As examples of temperature-stable test chemistries, reference can be made, for example, to WO 2007/012494 A1 which is already cited above and to WO 2010/094426 A1 and WO 2010/094427 A1 which are already cited above. The test chemistries presented therein are also usable in the context of the present invention, alone or else in combination with one or more other test chemistries.

For instance, the test chemistry can contain, for example, an enzyme and a stable coenzyme which are stored together. It was found that, surprisingly, with the aid of a stable coenzyme it is possible to have temperature stabilization and/or long-term stabilization lasting several weeks or months at high relative humidity or even in liquid phase and at elevated temperatures. This finding is surprising, since it is known that although enzymes in the presence of a native coenzyme have elevated short-term stability for a few hours, they exhibit a relatively short storage life over a prolonged period. With respect to these findings with respect to the prior art, it was surprising that an enzyme in the presence of a stable coenzyme has a distinctly elevated temperature stability and long-term stability than an enzyme in the presence of a native coenzyme, particularly since the stable coenzymes have a lower binding constant with the enzyme than the native coenzyme.

The enzyme stabilized by the process according to the invention can in particular be a coenzyme-dependent enzyme. Suitable enzymes are, for example, dehydrogenases selected from glucose dehydrogenase (E.C.1.1.1.47), lactate dehydrogenase (E.C.1.1.1.27, 1.1.1.28), malate dehydrogenase (E.C.1.1.1.37), glycerol dehydrogenase (E.C.1.1.1.6), alcohol dehydrogenase (E.C.1.1.1.1), alpha-hydroxybutyrate dehydrogenase, sorbitol dehydrogenase or amino acid dehydrogenase, for example L-amino acid dehydrogenase (E.C.1.4.1.5). Further suitable enzymes are oxidases, for example glucose oxidase (E.C.1.1.3.4) or cholesterol oxidase (E.C.1.1.3.6), or aminotransferases, for example aspartate or alanine aminotransferase, 5'-nucleotidase or creatine kinase. Preferably, the enzyme is glucose dehydrogenase.

It has been found to be particularly preferable to use a mutated glucose dehydrogenase. The term "mutant", as used in the context of the present application, means a genetically altered variant of a native enzyme which, while having the same number of amino acids, has an amino acid sequence which is altered with respect to the wild-type enzyme, i.e. differs from the wild-type enzyme by at least one amino acid. The mutation(s) can be introduced in a site-specific manner or a non-site-specific manner, preferably in a site-specific manner using recombinant methods known in the specialist field, resulting in at least one amino acid exchange within the amino acid sequence of the native enzyme according to the particular requirements and conditions. Particularly preferably, the mutant has increased thermal or hydrolytic stability with respect to the wild-type enzyme.

The mutated glucose dehydrogenase can contain the amino acid(s) altered with respect to the corresponding wild-type glucose dehydrogenase at, in principle, any desired position of its amino acid sequence. Preferably, the mutated glucose dehydrogenase comprises a mutation at at least one of positions 96, 170 and 252 of the amino acid sequence of the wild-type glucose dehydrogenase, particular preference being given to mutants having mutations at position 96 and position 170 or mutations at position 170 and position 252. It has been found to be advantageous for the mutated glucose dehydrogenase to contain no further mutations besides said mutations.

The mutation at positions 96, 170 and 252 can in principle comprise any desired amino acid exchange which results in stabilization, for example an increase in thermal or hydrolytic stability, of the wild-type enzyme. Preferably, the mutation at position 96 comprises an amino acid exchange from glutamic acid to glycine, whereas with regard to position 170, preference is given to an amino acid exchange from glutamic acid to arginine or lysine, more particularly an amino acid exchange from glutamic acid to lysine. Concerning the mutation at position 252, this preferably comprises an amino acid exchange from lysine to leucine.

The mutated glucose dehydrogenase can be obtained by mutation of a wild-type glucose dehydrogenase originating from any desired biological source, and in the context of this invention, the term "biological source" comprises not only prokaryotes, for example bacteria, but also eukaryotes, for example mammals and other animals. Preferably, the wild-type glucose dehydrogenase comes from a bacterium, particular preference being given to a glucose dehydrogenase from *Bacillus megaterium, Bacillus subtilis* or *Bacillus thuringiensis*, more particularly from *Bacillus subtilis*.

In a particularly preferred embodiment of the present invention, the mutated glucose dehydrogenase is a glucose dehydrogenase which is obtained by mutation of wild-type glucose dehydrogenase from *Bacillus subtilis* and which has the amino acid sequence presented in SEQ ID NO: 1 (GlucDH_E96G_E170K) or in SEQ ID NO: 2 (GlucDH_E170K_K252L).

The stable coenzyme is preferably a coenzyme which is chemically altered with respect to the native coenzyme and which has greater stability (e.g. hydrolytic stability) compared to the native coenzyme. Preferably, the stable coenyzme is stable under test conditions with respect to hydrolysis. Compared to the native coenzyme, the stable coenzyme can have a reduced binding constant for the enzyme, for example a binding constant reduced by a factor of 2 or more.

Preferred examples of stable coenzymes are stable derivatives of nicotinamide adenine dinucleotide (NAD/NADH) or nicotinamide adenine dinucleotide phosphate (NADP/NADPH), or truncated NAD derivatives, for example without the AMP part or with non-nucleosidic residues, for example hydrophobic residues. Likewise preferred as a stable coenzyme in the context of the present invention is the compound of the formula (I).

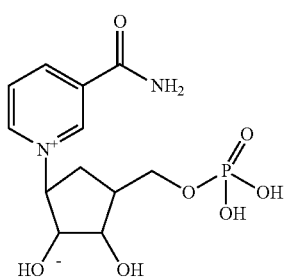

Preferred stable derivatives of NAD/NADH and NADP/NADPH are described in the previously mentioned references, the disclosure of which is hereby expressly incorporated by reference. Particularly preferred stabilized coenzymes are described in WO 2007/012494 and U.S. application Ser. No. 11/460,366, the disclosure of which is hereby expressly incorporated by reference. The stable coenzyme is particularly preferably selected from compounds having the general formula (II):

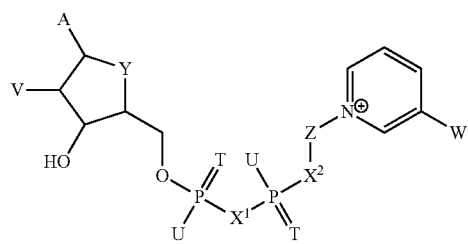

with

A=adenine or an analog thereof,

T=in each case independently O, S,

U=in each case independently OH, SH, $BH_3^-$, $BCNH_2^-$,

V=in each case independently OH or a phosphate group, or two groups which form a cyclic phosphate group;

W=COOR, $CON(R)_2$, COR, $CSN(R)_2$ with R=in each case independently H or $C_1$-$C_2$-alkyl, $X^1$, $X^2$=in each case independently O, $CH_2$, $CHCH_3$, $C(CH_3)_2$, NH, $NCH_3$,

Y=NH, S, O, $CH_2$,

Z=a linear or cyclic organic radical, with the proviso that Z and the pyridine residue are not linked by a glycosidic bond, or a salt or, where appropriate, a reduced form thereof.

In the compounds of the formula (II), Z is preferably a linear radical having 4-6 carbon atoms, preferably 4 carbon atoms, in which 1 or 2 carbon atoms are optionally replaced by one or more heteroatoms selected from O, S and N, or a radical comprising a cyclic group having 5 or 6 carbon atoms, which cyclic group optionally contains a heteroatom selected from O, S and N and optionally one or more substituents, and a radical $CR^4_2$, where $CR^4_2$ is bonded to the cyclic group and to $X^2$, with $R^4$=in each case independently H, F, Cl, $CH_3$.

Particularly preferably, Z is a saturated or unsaturated carbocyclic or heterocyclic five-membered ring, more particularly a compound of the general formula (III)

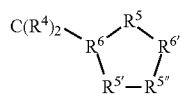
(III)

where a single or double bond can be present between $R^{5'}$ and $R^{5'''}$, with
$R^4$=in each case independently H, F, Cl, $CH_3$,
$R^5=CR^4_2$,
where $R^{5'}$=O, S, NH, $NC_1$-$C_2$-alkyl, $CR^4_2$, CHOH, $CHOCH_3$, and
$R^{5'''}=CR^4_2$, CHOH, $CHOCH_3$ if a single bond is present between $R^{5'}$ and $R^{5'''}$, and
where $R^{5'}=R^{5'''}=CR^4$ if a double bond is present between $R^{5'}$ and $R^{5'''}$, and
$R^6$, $R^{6'}$=in each case independently CH or $CCH_3$.

In a preferred embodiment, the compounds according to the invention contain adenine or adenine analogs, for example $C_8$- and $N_6$-substituted adenine, deaza variants such as 7-deaza, aza variants such as 8-aza or combinations such as 7-deaza or 8-aza or carbocyclic analogs such as formycin, and the 7-deaza variants can be substituted in position 7 by halogen, $C_1$-$C_6$-alkinyl, $C_1$-$C_6$-alkenyl or $C_1$-$C_6$-alkyl.

In a further preferred embodiment, the compounds contain adenosine analogs which, instead of ribose, contain, for example, 2-methoxydeoxyribose, 2'-fluorodeoxyribose, hexitol, altritol or polycyclic analogs, such as bicyclo-, LNA- and tricyclo-sugars.

More particularly, it is also possible in the compounds of the formula (II) for (di)phosphate oxygens to be replaced, for example to be replaced isotronically and/or isovalently and/or isoelectronically, for example $O^-$ by $S^-$ or $BH_3^-$, O by NH, $NCH_3$ or $CH_2$ and $=O$ by $=S$.

In the compounds of the formula (II) according to the invention, W is preferably $CONH_2$ or $COCH_3$.

In the groups of the formula (III), $R^5$ is preferably $CH_2$. In addition, it is preferred that $R^{5'}$ is selected from $CH_2$, CHOH and NH. In a particularly preferred embodiment, $R^{5'}$ and $R^{5'''}$ are each CHOH. In yet a further preferred embodiment, $R^{5'}$ is NH and $R^{5'''}$ is $CH_2$.

In the most strongly preferred embodiment, the stable coenzyme is carbaNAD as described, for example, inter alia in the document WO 2007/012494 already mentioned above.

The preferred test chemistry is in particular configured such that the enzymes contained therein are stabilized for a long time. This means that the enzyme stabilized using a stable coenzyme, for example in the form of a dry substance, is stored, for example, over a period of at least two weeks, preferably at least four weeks and particularly preferably at least eight weeks, with the enzymatic activity decreasing preferably by less than 50%, particularly preferably less than 30% and most preferably less than 20% with regard to the starting value of the enzymatic activity.

As a result of the stabilization according to the invention, it is possible for the enzyme stabilized using a stable coenzyme to be stored even without drying reagent for a long time, as indicated above, and/or at high temperatures, as indicated above. In addition, the stabilized enzyme can even be stored at a high relative humidity, for example a relative humidity of at least 50%, with the enzymatic activity decreasing preferably by less than 50%, particularly preferably less than 30% and most preferably less than 20% with regard to the starting value.

The enzyme stabilized using a stable coenzyme can be stored either as a dry substance or in liquid phase. Preferably, the stabilized enzyme is stored on or in a test element which is suitable for the determination of an analyte. The enzyme stabilized using a stable coenzyme is a constituent of the preferred test chemistry, which can optionally contain in addition further constituents such as, for example, salts, buffers, etc. Preferably, the test chemistry is free of a mediator.

The enzyme stabilized using a stable coenzyme can in general be used for the detection of analytes, for example parameters in body fluids such as, for example, blood, serum, plasma or urine or in waste water samples or foodstuffs. Analytes which can be determined are any desired biological or chemical substances which can be detected by a redox reaction, for example substances which are substrates of a coenzyme-dependent enzyme or coenzyme-dependent enzymes themselves. Preferred examples of analytes are glucose, lactic acid, malic acid, glycerol, alcohol, cholesterol, triglycerides, ascorbic acid, cysteine, glutathione, peptides, urea, ammonium, salicylate, pyruvate, 5'-nucleotidase, creatine kinase (CK), lactate dehydrogenase (LDH), carbon dioxide, etc. Preferably, the analyte is glucose. Particularly preferably, in this case, glucose is detected using glucose dehydrogenase (GlucDH).

The change in the stable coenzyme as a result of reaction with the analyte can in principle be detected in any desired manner. Here, it is possible in principle to use all methods known from the prior art for detecting enzymatic reactions. However, the change in the coenzyme is preferably detected by optical methods. Optical detection methods comprise, for example, the measurement of absorption, fluorescence, circular dichroism (CD), optical rotatory dispersion (ORD), refractometry, etc.

An optical detection method which is preferably used in the context of the present application is photometry. Photometric measurements of a change in the coenzyme because of reaction with the analyte require, however, the additional presence of at least one mediator which increases the reactivity of the reduced coenzyme and enables electrons to be transferred to a suitable optical indicator or an optical indicator system.

Mediators which are suitable for the purposes of the present invention are, inter alia, nitrosoanilines such as, for example, [(4-nitrosophenyl)imino]dimethanol hydrochloride, quinones such as, for example, phenanthrenequinones, phenanthrolinequinones or benzo[h]quinolinequinones, phenazines such as, for example, 1-(3-carboxypropoxy)-5-ethylphenazinium trifluoromethanesulphonate, and/or diaphorase (EC 1.6.99.2). Preferred examples of phenanthrolinequinones comprise 1,10-phenanthroline-5,6-quinones, 1,7-phenanthroline-5,6-quinones, 4,7-phenanthroline-5,6-quinones and N-alkylated or N,N'-dialkylated salts thereof, and in the case of N-alkylated or N,N'-dialkylated salts, preferred counterions are halides, trifluoromethanesulphonate or other anions which increase the solubility.

The optical indicator or optical indicator system used can be any desired substance which is reducible and, upon reduction, undergoes a detectable change in its optical properties, such as, for example, color, fluorescence, reflectance, transmission, polarization and/or refractive index. The presence and/or the amount of the analyte in the sample can be determined with the naked eye and/or by means of a detection device using a photometric method which appears to be suitable to a person skilled in the art. Preferably, heteropolyacids, and more particularly 2,18-phosphomolybdic acid, are used as optical indicators which are reduced to the corresponding heteropoly blue.

Particularly preferably, the change in the coenzyme is detected by measuring the fluorescence. Fluorescence measurement is highly sensitive and makes it possible to detect even low concentrations of the analyte in miniaturized systems.

Alternatively, the change in the coenzyme can also be detected electrochemically using a suitable test element, such as, for example, an electrochemical test strip. A prerequisite for this is again the use of suitable mediators which can be converted by the reduced coenzyme, via transfer of electrons, into a reduced form. The analyte is determined via measurement of the current required for the reoxidation of the reduced mediator, which current correlates with the concentration of the analyte in the sample. Examples of mediators which can be used for electrochemical measurements comprise in particular the above-mentioned mediators used for photometric measurements.

A particularly preferred test format comprises the use of the enzyme glucose dehydrogenase with a stable NAD derivative for the detection of glucose, forming a derivative of the reduced coenzyme NADH. NADH is detected by optical methods, for example by photometric or fluorometric determination following UV excitation. A particularly preferred test system is described in US 2005/0214891, to which express reference is made here.

More particularly, the stable test chemistry can be configured such that it comprises an enzyme stabilized using a stable coenzyme, with the stabilized enzyme exhibiting upon storage for preferably at least two weeks, particularly preferably at least four weeks and most preferably at least eight weeks at a temperature of preferably at least 20° C., particularly preferably at least 25° C. and most preferably at least 30° C., optionally at high humidity and without drying reagent, a decrease in enzymatic activity of less than 50%, preferably less than 30% and most preferably less than 20% with respect to the starting value.

As explained above, the test element can in particular comprise at least one support element, wherein the test chemistry is preferably connected to the support element. Said connection can, for example, be achieved by applying the test chemistry directly or indirectly in the form of at least one test chemistry layer to the support element, and this can, for example, also be carried out in the context of the above-described process step a). For example, application can be achieved by a process selected from the group consisting of knife-coating, printing (more particularly screen printing, stencil printing, pad printing) and spin-coating.

As described above, the support element can in particular be completely or partly produced from at least one plastics material. More particularly, said plastics material can be a plastics material having a softening temperature, determinable in accordance with DIN EN ISO 306, of at least 100° C., preferably at least 110° C. and particularly preferably at least 120° C., for example having a softening temperature of at least 130° C. or even at least 140° C. or at least 150° C. Examples of such plastics are acrylonitrile-butadiene-styrene (ABS), polymethyl methacrylate (PMMA), polypropylene (PP), polyester and polycarbonate (PC) or combinations of the aforementioned and/or other plastics. However, other plastics are also usable in principle. More particularly, the housing part to which the test element is connected during the shaping process can be completely or partly produced from such a plastics material as housing material.

The support element can in particular comprise at least one film element, and with regard to the film element, reference can be made to the above definition. More particularly, in this case, it can be a plastics film. Said film can have a single-layer or else multilayer structure. The support element can support one or more test chemistries. Furthermore, the support element can, alternatively or in addition, support the at least one test chemistry for a plurality of analytical aids. For example, a support element for a plurality of analytical aids can be provided, and so a plurality of analytical aids shares one support element or parts thereof. For example, the support element can support a continuous test chemistry, with different surface regions of said test chemistry forming test field areas for different analytical aids. For example, a support film can be provided which is coated extensively with test chemistry, with at least one first region of a surface of the test chemistry being provided for a first analytical aid, and at least one second region of the surface as test field area being provided for at least one second analytical aid. As an alternative to a continuous test chemistry layer providing test field areas for a plurality of analytical aids, it is also possible to provide different test chemistry layers, for example by applying a plurality of adjacent test chemistry layers to one support element, for example by a printing process, a knife-coating process, a dispenser process, a spin-coating process or another coating process, it being possible for the plurality of test chemistry layers to provide in each case test field areas for one or more analytical aids. For example, it is possible to provide a common support film onto which at least one first test chemistry layer and at least one second test chemistry layer are printed side by side, with the first test chemistry layer providing with its surface at least one first test field area for at least one first analytical aid and with the second test chemistry layer providing with its surface at least one second test field area for at least one second analytical aid.

The support element can in particular be a disc-shaped support element. For example, the support element can be in the form of a rectangular, polygonal or round disc. As described in more detail below, particular preference is given to the use of at least one strip-shaped support element and/or at least one ring-shaped support element (for example at least one circular-ring-shaped support element) and/or at least one circular-disc-shaped support element. For example, circular-ring-shaped support elements can be produced. The test chemistry can be applied to the support element as a coating, wherein the coating provides test field areas for the analytical aids. The analytical aids can, for example, be arranged concentrically around the center of the disc, more particularly the circular disc and particularly preferably the circular-ring-shaped disc.

The housing part can in particular be at least partly produced from at least one housing material which is preferably selected from the group consisting of: a polycarbonate; a polyester; an acrylonitrile-butadiene-styrene, a cyclo-olefin copolymer; a polymethyl methacrylate; a polystyrene; a polyethylene terephthalate.

As described above, the process can be carried out such that exactly one analytical aid is produced. However, particularly preferably, the process can be carried out such that a plurality of analytical aids is produced. The process can preferably be carried out such that a plurality of analytical aids is produced, with the analytical aids being contained in an analytical magazine. The expression "are contained" is generally to be understood to mean the possibility that the analytical aids are, for example, accommodated in an outer shell of the magazine, for example in an interior space of the magazine. However, alternatively or in addition, the analytical aids can also be contained in the magazine such that they are fixed constituents of the magazine, for example by the analytical aids being firmly, more particularly rigidly, connected to one another and by, for example, the housing parts of the analytical aids being constituents of a magazine housing of the magazine.

The analytical aids of a magazine can, for example, be produced simultaneously. This can, for example, be achieved by simultaneously producing the housing parts of the analytical aids, which are preferably also simultaneously connected to one another, during the above-described shaping process, for example during the plastics shaping process. This can, for example, be achieved by the housing parts being produced in one and the same mold cavity and/or in different mold cavities of one and the same mold. If a plurality of mold cavities is provided for the housing parts, they are, for example, fluidically connected to one another, and so they can, for example, be connected to one another by the housing material during a shaping process.

The analytical aids can in particular be accommodated in a common magazine housing. The process can in particular be carried out such that the housings of the analytical aids are constituents of the magazine housing.

In a further aspect of the present invention, there is proposed an analytical aid for the detection of at least one analyte in a sample, more particularly a liquid sample and particularly preferably a sample of a body fluid. The analytical aid can in particular be obtainable in a process according to one or more of the embodiments described above or to be described below. Accordingly, for possible embodiments of the analytical aid, reference can be made to the possible embodiments of the process, and vice versa. The analytical aid comprises at least one housing comprising at least one housing part and at least one test element. The test element can, for example, be configured according to the above description and can in particular comprise at least one support element. In addition, the test element comprises at least one test chemistry. The test element is connected to the housing part by means of a shaping process of the housing part.

For further possible embodiments, reference can be made to the above or below description, more particularly the description of the process. For instance, the test element can in particular be connected to the housing part such that the test element rests on the housing part at at least one surface area. The test element can in particular be at least partly embedded in the housing part. The test element can in particular be connected to the housing part in a manner selected from the group consisting of a cohesive bond.

The test element can in particular be connected to the housing part in a manner selected from the group consisting of: a cohesive bond, a form-fit connection, and a force-fit connection. The housing part can in particular comprise at least one housing material, with the housing material preferably comprising at least one plastics material, for example one or more of the above-mentioned plastics materials. The test element can in particular be connected to the housing part by in-mold coating and/or overmolding. The test element can in particular be connected to the housing part such that part of the test chemistry is exposed, for input of the sample, it being possible for said part of the test chemistry to form, for example, at least one test field area. For possible embodiments of the test field area, reference can be made to the above description. More particularly, the test element can be connected to the housing part such that at least one surface of the test chemistry as test field area for input of the sample remains uncovered by a housing material of the housing part, i.e. is not covered with housing material of the housing part. The housing can in particular be configured such that at least one observation window is formed in the housing, wherein the test field area is optically monitorable through the observation window of the housing, more particularly from outside of the housing. The housing can in particular comprise at least one chamber, wherein the test field area preferably faces an interior space of the chamber. In addition, the analytical aid can comprise at least one lancet element, for example at least one lancet element which is accommodated in a chamber, more particularly at least one microsampler.

Thus, the test element can in particular be connected to the housing part directly, i.e. without interposition of one or more connecting elements and/or connecting materials. More particularly, the test element can be connected to the housing part free of adhesive. The test element can in particular be at least partially embedded in the housing part, and with regard to the various possibilities, reference can be made to the above description.

The analytical aid can in particular comprise at least one chamber, with the test element comprising at least one test field area facing the chamber, i.e. a surface of the test chemistry, with the test field area being accessible from the chamber for input of the sample. The test field area can in particular be configured such that it is at least framed in part by a wall of the chamber, for example is at least overlapped in part by a wall of the chamber, it being possible for the wall of the chamber to rest, for example, on the test field area.

Furthermore, the housing can, alternatively or in addition, comprise at least one observation window, wherein the test field area is optically monitorable through the observation window of the housing. For possible embodiments, reference can be made to the above description.

As explained above, the analytical aid can, in addition to the at least one test chemistry, further comprise at least one lancet element for generating the sample, more particularly at least one microsampler. The lancet element can, for example, be mounted movably with respect to the housing, for example in the housing, more particularly in at least one chamber of the housing. The movable mounting can in particular be configured such that the lancet element can carry out at least one lancet movement, i.e. a movement in which the sample is generated. Said lancet movement can, for example, be achieved in a lancet direction in which at least one tip and/or blade of the lancet element leaves the chamber, for example through an appropriate opening. The lancet movement can, for example, be driven by an actuator which can be a constituent of the analytical aid or a separate device. For example, for this purpose, it is possible for at least one actuator to act on the lancet at one end facing away from the lancet tip or lancet blade. Said actuator can, for example, enter the chamber of the analytical aid through an actuator opening. The actuator can, for example, be driven by an appropriate spring mechanism. With regard to possible embodiments of such actuators, which are known in principle to a person skilled in the art, reference can be made to the prior art.

The analytical aid can in particular be designed such that the lancet element is movable back into the housing after the lancet movement has been carried out. For this purpose, the lancet can comprise, for example, at least one coupling element which is coupleable to an actuator, it being possible to carry out by means of the actuator a lancet movement and a remagazination movement in a direction opposite to the lancet movement, it being possible during remagazination for the lancet element to be mounted in the housing again. During or after the return movement, the sample taken up by the lancet element can be transferable to the test element. Said transfer can be achieved in various ways. For example, the lancet element, for example the microsampler, can be guided close to the test element, more particularly to a test field area of the test element, such that the sample is transferred to the test field area. Alternatively or in addition, it is also possible to provide at least one further actuator which brings about the transfer, for example by pressing the lancet element onto the test field area. Alternatively or in addition, it is in turn also possible, for example, to shape the housing such that, during the return movement of the lancet element into the housing, i.e. for example during the remagazination movement, the lancet briefly approaches the test field area, and so a transfer takes place. This can, for example, be brought about by an appropriately curved guide of the lancet element in the housing.

As explained above, the analytical aid can in particular be configured such that the housing comprises at least one observation window accessible from an outer side of the housing. At least one property change of the test element, more particularly at least one color change and/or at least one change in at least one optical property, can be detectable from outside through the observation window. For possible embodiments of the observation window, reference can be made to the above description. The observation window can in particular be at least partly surrounded by a frame of the housing, more particularly the housing part. Said frame can, for example, rest directly on the test element. As described above, the observation window can in particular be configured such that it is possible to optically monitor the test chemistry through the observation window and through at least one support element of the test element. Thus, the observation window can in particular be configured such that at least one test field area of the test element is observable through at least one support element, which is at least partially optically transparent, of the test element. In this case, observation is to be understood to mean, for example, detection of at least one optical property change of the test chemistry.

In a further aspect of the present invention, there is proposed an analytical magazine comprising a plurality of analytical aids according to one or more of the above-described embodiments or according to one or more of the exemplary embodiments to be described below. The analytical aids can in particular be connected firmly to one another. More particularly, the analytical aids can be connected rigidly to one another, and so the relative position thereof is fixed. More particularly, the analytical magazine can comprise a magazine housing, it being possible for the housings of the analytical aids, more particularly the housing parts, to be constituents of the magazine housing. For example, the housing parts of the analytical aids can be sections of the magazine housing which are adjacent to one another or connected to one another in another way.

The analytical magazine can in particular be in the form of a circular disc and/or in the form of a circular ring, with the analytical aids being, for example, arranged radially in the analytical magazine. However, as an alternative or in addition to the form of a circular ring, other forms are also possible, for example a disc form, a bar form, a strip form or other forms.

In summary, the following embodiments are particularly preferred in the context of the present invention:

Embodiment 1

Process for producing an analytical aid for the detection of at least one analyte in a sample, more particularly a body fluid, wherein the analytical aid comprises at least one housing and at least one test element comprising at least one test chemistry, wherein the process comprises the following steps:
a) providing the test element; and
b) producing at least one housing part of the housing by means of at least one shaping process, during which the test element is connected to the housing part.

Embodiment 2

Process according to the preceding embodiment, wherein, during the shaping process, the test chemistry in at least one section of the test element is contacted with at least one housing material of the housing part, with the test chemistry in at least one further section of the test element remaining free of the housing material.

Embodiment 3

Process according to any of the preceding embodiments, wherein, during the shaping process, the test element is connected to the housing part such that the test element rests on the housing part at at least one surface area.

Embodiment 4

Process according to any of the preceding embodiments, wherein, during the shaping process, the test element is at least partly embedded in the housing part.

Embodiment 5

Process according to any of the preceding embodiments, wherein the test element is connected to the housing part in a manner selected from the group consisting of a cohesive bond, a form-fit connection and a force-fit connection.

Embodiment 6

Process according to any of the preceding embodiments, wherein the shaping process comprises at least one casting process, more particularly a plastics casting process.

Embodiment 7

Process according to any of the preceding embodiments, wherein the shaping process comprises at least one plastics shaping process.

Embodiment 8

Process according to the preceding embodiment, wherein the plastics shaping process is selected from the group consisting of: a casting process, more particularly an injection-molding process; a compression process, more particularly a transfer-molding process.

Embodiment 9

Process according to either of the two preceding embodiments, wherein the plastics shaping process is selected from in-mold coating and overmolding.

Embodiment 10

Process according to any of the preceding embodiments, wherein, in process step b), at least part of the test element is inserted into a shaping mold and is at least partly contacted, in the shaping mold, with at least one housing material of the housing part, more particularly is enveloped by at least one housing material of the housing part.

Embodiment 11

Process according to the preceding embodiment, wherein the at least one test element part inserted into the shaping mold rests, via at least one section, on at least one wall of the shaping mold.

Embodiment 12

Process according to the preceding embodiment, wherein process step b) is carried out such that the wall of the shaping mold, at least in the region on which the section of the test element rests on the wall, has a temperature of not more than 130° C., preferably not more than 120° C. and particularly preferably not more than 110° C. while process step b) is being carried out.

Embodiment 13

Process according to any of the three preceding embodiments, wherein the section of the test element which rests on the wall comprises at least part of the test chemistry, more particularly a test field area of the test chemistry.

Embodiment 14

Process according to any of the preceding embodiments, wherein the shaping process is carried out free of release agent.

Embodiment 15

Process according to any of the preceding embodiments, wherein, in process step b), the test element is connected to the housing part such that at least one surface of the test chemistry as test field area for input of the sample remains uncovered by a housing material of the housing part.

Embodiment 16

Process according to the preceding embodiment, wherein the housing is configured such that at least one observation window is produced in the housing, wherein the test field area is optically monitorable through the observation window of the housing.

Embodiment 17

Process according to either of the two preceding embodiments, wherein the process is carried out such that the housing forms at least one chamber, wherein the test field area faces an interior space of the chamber.

Embodiment 18

Process according to the preceding embodiment, wherein the process comprises in addition at least one process step in which at least one lancet element for generating the sample is introduced into the chamber, more particularly at least one microsampler.

Embodiment 19

Process according to any of the preceding embodiments, wherein the test chemistry is selected in terms of stability such that it is stable, at least for a short time, with respect to temperatures of 100° C., more particularly with respect to temperatures of 110° C. and particularly preferably with respect to temperatures of 120° C.

Embodiment 20

Process according to any of the preceding embodiments, wherein the test element comprises at least one support element, wherein the test chemistry is connected to the support element, more particularly by applying at least one layer of the test chemistry to the support element.

Embodiment 21

Process according to the preceding embodiment, wherein the support element is completely or partly produced from at least one plastics material, more particularly a plastics material having a softening temperature, determinable in accordance with DIN EN ISO 306, of at least 100° C., preferably at least 110° C. and particularly preferably at least 120° C.

Embodiment 22

Process according to either of the two preceding embodiments, wherein the support element comprises at least one film element, more particularly at least one plastics film.

Embodiment 23

Process according to any of the three preceding embodiments, wherein the support element supports the test chemistry for a plurality of analytical aids.

Embodiment 24

Process according to the preceding embodiment, wherein the support element is a disc-shaped support element, more particularly a circular-disc-shaped support element and particularly preferably a circular-ring-shaped support element, wherein the test chemistry is applied to the support element as a coating, wherein the coating provides test field areas for the analytical aids.

Embodiment 25

Process according to any of the preceding embodiments, wherein the housing part is at least partly produced from at least one housing material selected from the group consisting of: a polycarbonate; a polyester; an acrylonitrile-butadiene-styrene; a cyclo-olefin copolymer; a polymethyl methacrylate; a polystyrene; a polyethylene terephthalate.

Embodiment 26

Process according to any of the preceding embodiments, wherein a plurality of analytical aids is produced, wherein the process is carried out such that the analytical aids are contained in an analytical magazine.

Embodiment 27

Process according to the preceding embodiment, wherein the analytical aids are produced simultaneously.

Embodiment 28

Process according to either of the two preceding embodiments, wherein the analytical aids are accommodated in a common magazine housing.

Embodiment 29

Process according to the preceding embodiment, wherein the process is carried out such that the housings of the analytical aids are constituents of the magazine housing.

Embodiment 30

Analytical aid for the detection of at least one analyte in a sample, more particularly obtainable in a process according to any of the preceding embodiments, wherein the analytical aid comprises at least one housing comprising at least one housing part and at least one test element comprising at least one test chemistry, wherein the test element is connected to the housing part by means of a shaping process of the housing part.

Embodiment 31

Analytical aid according to the preceding embodiment, wherein the test element is directly connected to the housing part.

Embodiment 32

Analytical aid according to any of the preceding embodiments relating to an analytical aid, wherein the test element is at least partially embedded in the housing part.

Embodiment 33

Analytical aid according to any of the preceding embodiments relating to an analytical aid, wherein the analytical aid comprises at least one chamber, wherein the test element has at least one test field area facing the chamber, wherein the test field area is accessible from the chamber for input of the sample.

Embodiment 34

Analytical aid according to the preceding embodiment, wherein the test field area is configured such that it is at least partly framed by a wall of the chamber, wherein the wall of the chamber rests on the test field area.

Embodiment 35

Analytical aid according to any of the preceding embodiments relating to an analytical aid, wherein the analytical aid comprises in addition at least one lancet element for generating the sample, more particularly at least one microsampler.

Embodiment 36

Analytical aid according to the preceding embodiment, wherein the lancet element is mounted movably with respect to the housing, more particularly in at least one chamber, wherein the movable mounting is configured such that the lancet element can carry out at least one lancet movement.

Embodiment 37

Analytical aid according to the preceding embodiment, wherein the analytical aid is designed such that the lancet element is movable back into the housing after the lancet movement has been carried out, more particularly remagazinable, wherein, during or after the return movement, the sample taken up by the lancet element is transferable to the test element.

Embodiment 38

Analytical aid according to any of the preceding embodiments relating to an analytical aid, wherein the housing comprises at least one observation window accessible from an outer side of the housing, wherein at least one property change of the test element, more particularly at least one color change and/or at least one change in at least one optical property, is detectable from outside through the observation window.

Embodiment 39

Analytical aid according to the preceding embodiment, wherein the observation window is at least partly surrounded by a frame of the housing, more particularly the housing part.

Embodiment 40

Analytical aid according to either of the two preceding embodiments, wherein the observation window is configured such that at least one test field area of the test element is observable through at least one support element, which is at least partially optically transparent, of the test element.

Embodiment 41

Analytical magazine comprising a plurality of analytical aids according to any of the preceding embodiments relating to an analytical aid.

Embodiment 42

Analytical magazine according to the preceding embodiment, wherein the analytical magazine comprises a magazine housing, wherein the housings of the analytical aids are constituents of the magazine housing.

Embodiment 43

Analytical magazine according to either of the two preceding embodiments, wherein the analytical magazine is in the form of a circular ring, wherein the analytical aids are arranged radially in the analytical magazine.

The process proposed in the context of the present invention, the analytical aid and the analytical magazine have a multitude of advantages over known processes and devices. More particularly, the above-described disadvantages of known processes and devices can be at least substantially avoided. In addition, the process can also be carried out very cost-effectively and efficiently, since a multitude of work steps with respect to conventional production processes can be omitted. More particularly, application of an adhesive to housing parts and/or to the test element can be omitted if the test chemistry is provided preferably as a continuous piece, for example in the form of a test element comprising an elongated strip for a planar magazine in a straight arrangement and/or in a cylinder having an arrangement for test fields at the circumference, or as a ring for a magazine in a round disc arrangement, and connected to the housing part. More particularly, the test element can be inserted into an injection mold as an insert and overmolded with the housing material of the housing, preferably the magazine housing. In this process, an observation window, i.e. generally an observation region, for the particular test field area preferably remains free, it being possible, for example, to use a support film of the test element as a measurement window. Thus, the shaping process, more particularly the plastics shaping process and particularly preferably the injection-molding process, need not have any optical qualities. The test chemistry can even, in principle, be combined with a housing material in the form of a blackened material, for example overmolded, and this can in particular facilitate the suppression of scattered light during a measurement. Accordingly, the housing material can preferably be an optically nontransparent material, for example blackened material, preferably with a transparency of less than 5%, more particularly less than 1% and particularly preferably less than 0.5%, for example in the spectral range of from 400 nm to 800 nm.

The test element, for example with a continuous piece of a test chemistry, can, for example, either be subjected to in-mold coating on one side, and so preferably the full area of the actual test chemistry remains layer-free, or—for example if the wall thicknesses on both sides of the support element are sufficiently thick to permit an injection-molding procedure (for example ≥0.4 mm)—the test chemistry layer can be exposed only in the individual test field areas, and the spaces between the test field areas can be completely filled with plastic and/or surrounded by plastic.

Particularly the above-described preferred test chemistry, which is also referred to as cNAD test chemistry, is especially suitable for the proposed process and the proposed devices, since it withstands, at least for a short time, temperatures of typically up to 120° C. The processing temperatures of the plastics typically usable for the proposed analytical aids and analytical magazines are generally indeed above 120° C. However, those regions which must be available and operative afterwards as test chemistry, viz. the test field areas, are preferably in contact, during the proposed process, with a distinctly cooler mold wall, for example a mold wall which reaches a maximum temperature of 110° C., since they should remain free of housing material, for example injection-mold composition.

Since such moldings of medical consumable materials should typically be generally free of mold release agents, any contamination of the test chemistry with foreign substances is also generally not to be feared.

As explained above, the test element can, for example, comprise at least one support element, for example at least one support film. For example, support films composed of polycarbonate and/or a polyester can be used. It is possible to use, for example, a polycarbonate as housing material as well, or a material which is identical or at least chemically similar to the support element can be used in principle for the at least one housing part. In this way, it is possible to ensure a good connection between the support element, for example as insert, and the housing part, for example as injection molding.

A further advantageous aspect is that, in the case of miniaturized measurement systems, the summed and typically unavoidable variations in dimension must generally only be very small, since otherwise an optical measurement unit, for example, which has to work on a short working distance, does not have the object (for example the test field area and/or the test chemistry) in focus in every case. For instance, typical depths of focus of optical detection systems are maximally ±0.15 mm. In the case of a mounted test chemistry, there are not only the unavoidable mold-unrelated dimensions, but also generally the thickness of the adhesive typically used and the thickness of the support film, whose likewise unavoidable variations across the series can easily exceed the still available depth of focus of an optical measurement unit. All the same, in the case of conventional instruments, installation clearance must also remain in the instrument itself, including the optical measurement unit which itself typically does not remain free of variations in measurements. These disadvantages of conventional miniaturized measurement systems can be avoided or at least markedly reduced by the analytical aid according to the invention and the analytical magazine according to the invention. For example, in the case of direct overmolding or in-mold coating of the test element, generally only the mold-unrelated dimension of magazine thickness remains, which can typically be kept constant within still compatible limits, for example with a tolerance of ±0.05 mm, and so for the instrument, typically ±0.1 mm of tolerance for variations in dimension still remains. In connection with the term "mold-unrelated dimensions", it should be pointed out that this is generally a dimensional chain which reaches from the outside of the magazine towards the test chemistry arranged inside the magazine. Therefore, said dimensional chain generally includes dimensions which only arise with the interaction of a plurality of moldings of the magazine, for example two molded halves of the magazine. In this connection, all structures resulting from the mold structures of the shaping process which are worked directly into the mold wall can, for example, be referred to as mold-related. In contrast, all structures arising from the interaction of different mold walls which are movable against one another can be referred to as mold-unrelated. Such mold-unrelated structures generally bear not only the variations in mold production, the variability of the molding compound and the effects of the shaping process, but also generally a clearance which is required for the ability of the mold parts to move against one another and generally the effects of a shaping machine which drives the constituents of the shaping mold, for example the mold halves, together and apart. Mold-unrelated dimensions must generally be conceded larger tolerances.

Disc-shaped analytical magazines can be configured in particular according to the invention. These can in particular comprise one or more microsamplers. In addition, the test field areas of the test chemistries can form test fields, for example at least one test field per analytical aid, with the test fields being, for example, mounted firmly in the housing of the analytical aid and/or in the magazine housing. The at least one optional lancet element, which can be contained in the analytical aid, can be arranged movably with respect to it. Fixing the test field in the housing can, for example, be carried out by overmolding and/or in-mold coating of the test element during the shaping process, for example during the injection-molding process, in a simple or reliable manner. Such shaping processes, more particularly plastics shaping processes, are already nowadays typically used for the production of housings of analytical aids and/or of analytical magazines, and so standard processes can be further used with only slight modifications. More particularly, test chemistry rings can be used as test elements which are subjected to overmolding or in-mold coating. The above-described thermal stability of the proposed test chemistry, more particularly up to a temperature of 120° C., is noticeably especially favorable in this context.

Compared to the processes known from the prior art, in which chemistry fields are typically connected to at least one support via at least one adhesive, it is possible in the context of the present invention to completely dispense with adhesive materials. More particularly, a connection between the housing part and the test element can be achieved free of adhesive.

Such adhesive materials and adhesives often result in evaporations which not only can be damaging to the test element and, more particularly, the test chemistry therein, but also, more particularly, can destroy the hydrophilic coating of a microsampler, and so subsequently it is not possible, or is only possible with great difficulty, to ensure blood collection or another type of collection of body fluid. In this way, the preferred adhesive-free embodiment can also distinctly improve the quality and reliability of the analytical aids.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE SEVERAL VIEWS OF THE DRAWINGS

Further details and features of the invention will become apparent from the following description of preferred exemplary embodiments, particularly in connection with the dependent claims. In this case, the respective features can be realized on their own or as a plurality in combination with one another. The invention is not restricted to the exemplary embodiments. The exemplary embodiments are shown diagrammatically in the figures. Identical reference numbers in the individual figures designate identical elements or elements which are functionally identical or correspond to one another in terms of their functions.

In detail.

Figure 1:
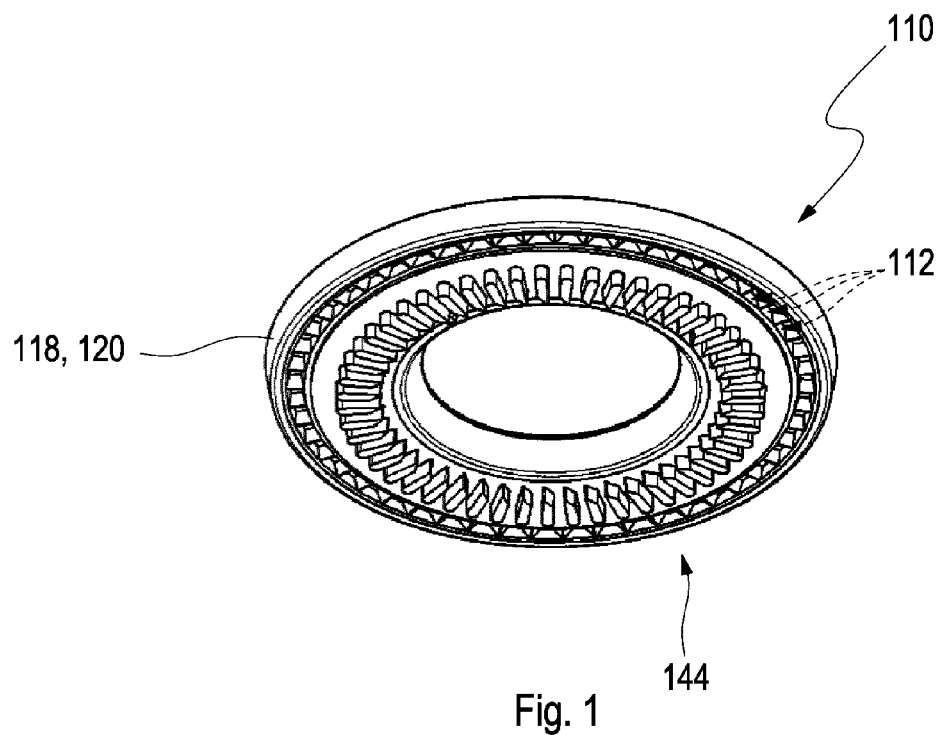
FIG. 1 shows a perspective view of an analytical magazine according to the invention comprising a plurality of analytical aids.

Skilled artisans will appreciate that elements in the drawings are illustrated for simplicity and clarity and have not necessarily been drawn to scale. For example, the dimensions of some of the elements in the drawing figures may be exaggerated relative to other elements to help improve understanding of the embodiments of the present invention.

DETAILED DESCRIPTION OF THE INVENTION

For the purposes of describing and defining the present invention it is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

FIGS. 1 to 7 show various diagrams of an exemplary embodiment of an analytical magazine 110 according to the invention. The analytical magazine 110 in the exemplary embodiment shown is a circular-ring-shaped or circular-disc-shaped analytical magazine 110 and comprises a plurality of analytical aids 112 which are arranged in a radial arrangement in the analytical magazine 110.

Figure 2:
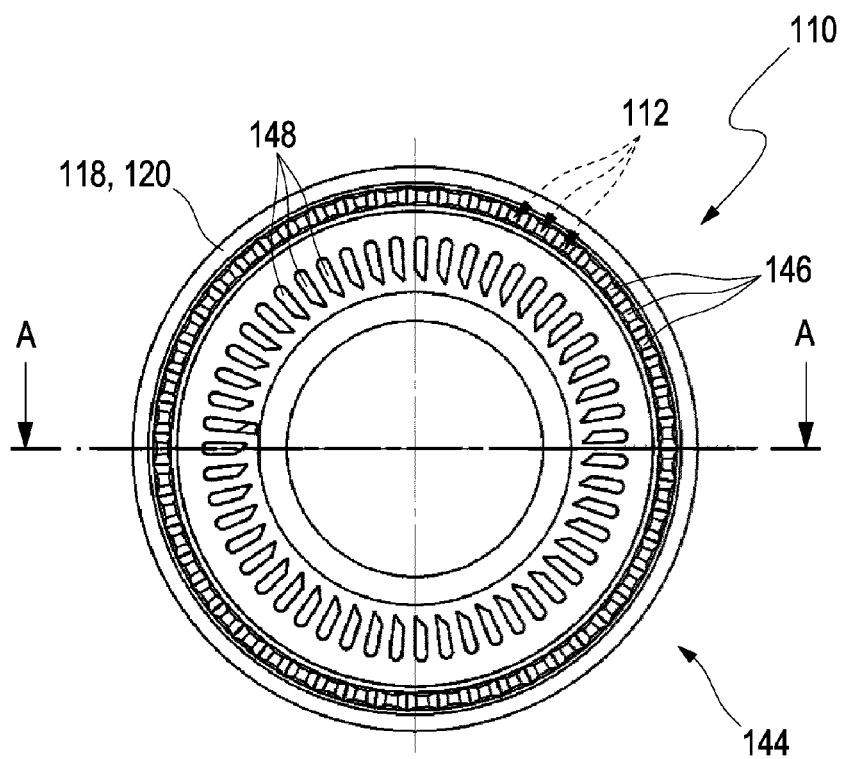
FIG. 2 shows an aerial view of the analytical magazine according to FIG. 1.
Figure 3:
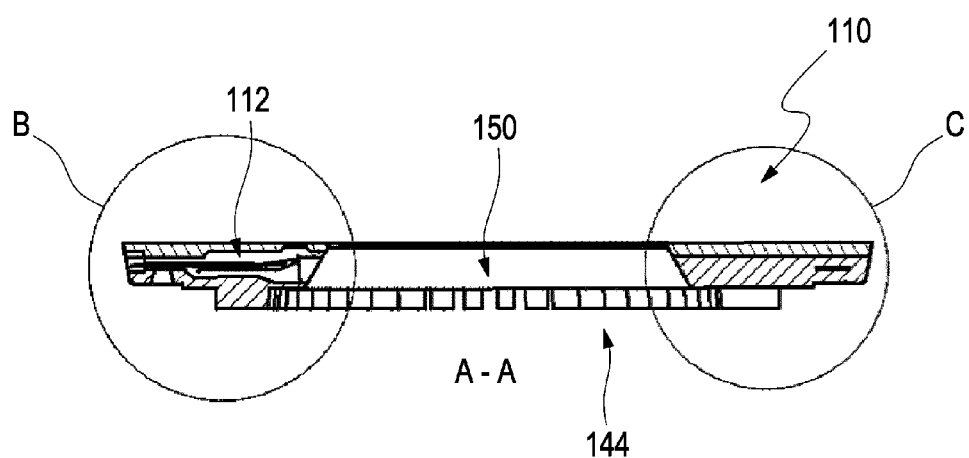
FIG. 3 shows a cross-sectional view through the analytical magazine along the intersecting line A-A in FIG. 2.
Figure 4:
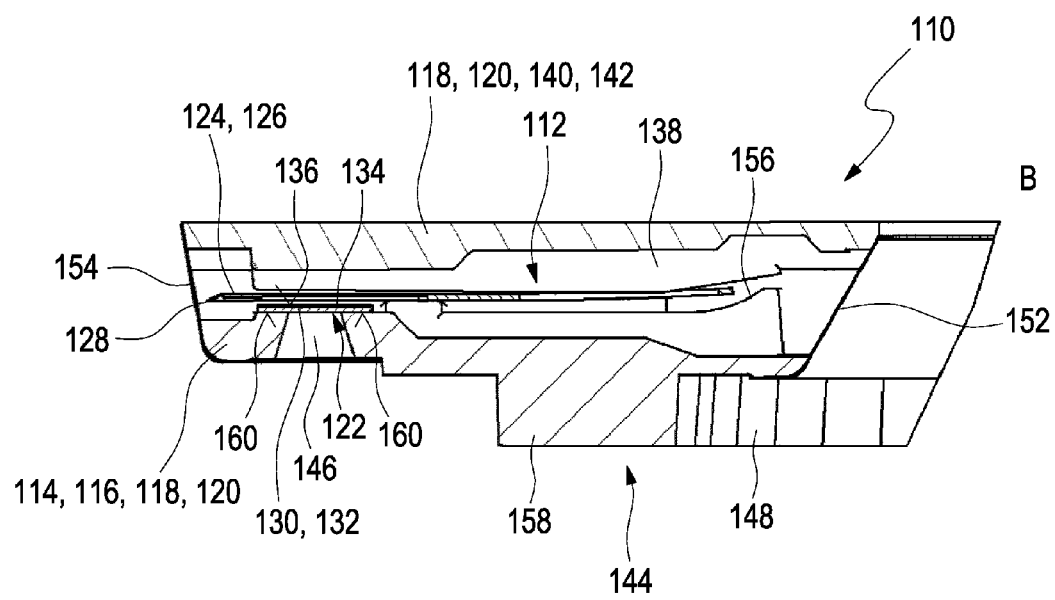
FIG. 4 shows an enlarged detailed view of region B in FIG. 3.
Figure 5:
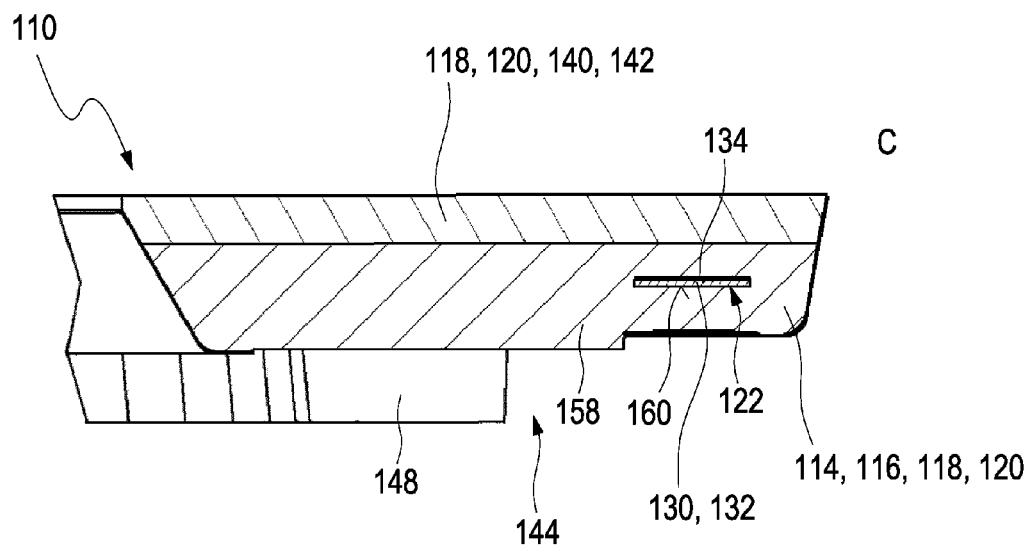
FIG. 5 shows an enlarged detailed view of region C in FIG. 3.
Figure 6:
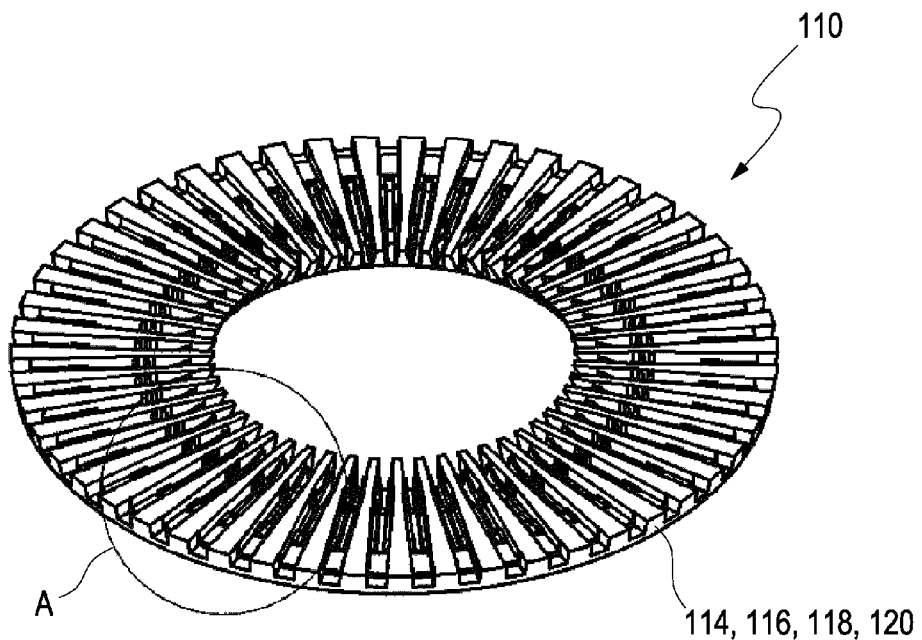
FIG. 6 shows a perspective view of a magazine housing lower part of the analytical magazine in FIGS. 1 to 5.
Figure 7:
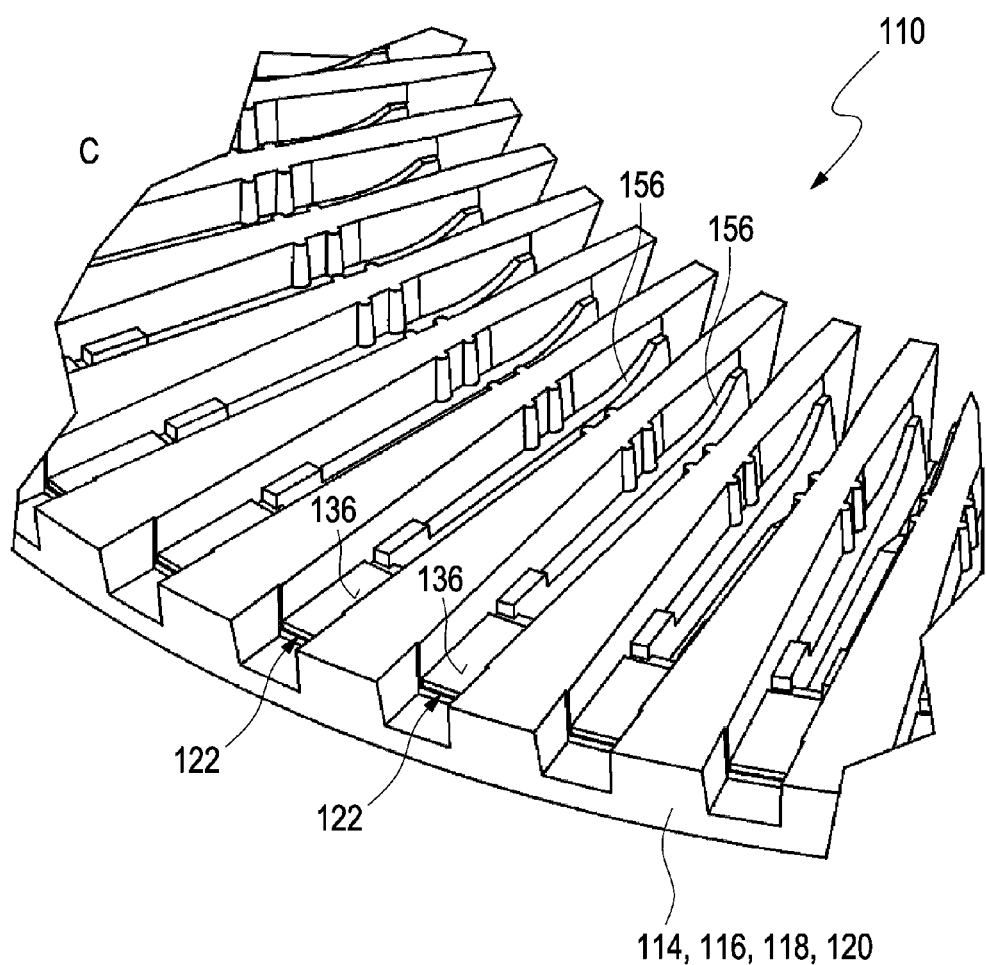
FIG. 7 shows an enlarged detailed view of region A in FIG. 6.

FIG. 1 shows a perspective view of the analytical magazine 110, FIG. 2 shows an aerial view of the analytical magazine 110, of a detection side, and FIG. 3 shows a cross-sectional view along an intersecting line A-A in FIG. 2. FIGS. 4 and 5 show enlarged detailed views of regions B and C, respectively, in the cross-sectional view according to FIG. 3. FIG. 6 shows an individual view of a housing part 114 of the analytical magazine in the form of a lower part 116 of a magazine housing 118, which lower part 116 combines housings 120 of the analytical aids 112. FIG. 7 shows an enlarged detailed view of cut-out A in FIG. 6. All the diagrams are described together below.

In the exemplary embodiment shown, the analytical aids 112 each comprise, as can especially be seen from the diagram in FIG. 4, at least one test element 122 and optionally at least one lancet element 124, which can in particular be a microsampler 126 and which, for example, can comprise, on a side facing downwards in FIG. 4, a capillary channel extending from a lancet tip 128, which capillary channel is not shown in more detail in the figures. The test elements 122 comprise a support element 130, for example a support film 132, onto which one or more layers of a test chemistry 134 are applied. The test chemistry 134 faces the lancet element 124 and forms in this region at least one test field area 136, onto which the liquid sample can be applied.

In the exemplary embodiment shown, at least one test field area 136 and at least one lancet element 124 are, in each case, optionally accommodated in a chamber 138, which is formed in the housing 120. Thus, an analytical aid 112 comprises, in each case, not only at least one test element 122 having a test field area 136 arranged in the chamber 138 and at least one lancet element 124, but also at least one housing 120 which forms the chamber 138. The housings 120 of the analytical aids 112 of the analytical magazine 110 are connected to one another and form common constituents of the magazine housing 118. In the exemplary embodiment shown, the housings 120 and the magazine housing 118 are, in each case, in multiple parts. Thus, the housings 120 each comprise housing parts 114, which are constituents of a lower part 116 of the magazine housing 118, and further housing parts 140, which are constituents of an upper part 142 of the magazine housing 118.

As described above, the chambers 138 are arranged radially in the circular-ring-shaped analytical magazine 110. FIGS. 6 and 7 show these radial arrangements, though these diagrams show, in each case, only the housing parts 114 of the housings 120 of the analytical aids 112 and the lower part 116 of the magazine housing 118. The lancet elements 124 are not shown in these diagrams.

As, for example, shown in the detailed view according to FIG. 4, the magazine housing 118 has, on the underside in FIG. 4, a detection side 144 on which observation windows 146 in the form of openings are formed in each case in the lower part 116 and in the housing parts 114. Said observation windows 146 are also discernible in the aerial view of the detection side 144 in FIG. 2. The support elements 130 of the test elements 122 are discernible through said observation windows 146. As will be explained in more detail below, said support elements 130 are preferably transparent, and so optical detection of an optical property change of the test chemistry 134 of the particular test element 122 is observable through the observation windows 146.

The analytical magazine 110 comprises, for example on the detection side 144, preferably a plurality of transport elements 148, by means of which a test instrument which uses the analytical magazine 110 can bring, in each case, exactly one analytical aid 112 into an application position. In said application position, it is possible, for example, for an actuator not shown in the figures to intrude into the chamber 138 through a central recess 150 in the analytical magazine 110 (see FIG. 3) through a proximal opening 152, also referred to as an actuator opening. There, the actuator can, for example, grasp a proximal end of the lancet element 124, for example a grommet arranged there and/or another type of connecting element. Then, the actuator can drive the lancet element 124 towards a lancet movement directed outwards in a radial manner (in FIG. 4, directed leftwards), with the lancet tip 128 leaving the chamber 138 through a distal opening 154, making a prick or cut in a user's skin and taking up a liquid sample, preferably using the capillary element. Subsequently, the actuator can be arranged to carry out remagazination of the lancet element 124, for example by the lancet element 124 being drawn back into the chamber 138 in which the lancet element 124 had previously been stored.

Subsequently, a sample can be transferred to the test field area 136 of the test element 122. This can, for example, be achieved by the lancet element approaching the test field area 136 very closely for a short time, for example by means of an appropriate shaping of the walls of the chamber 138. For example, it is possible for this purpose to provide one or more appropriate contours 156 in the housing part 114, as is, for example, discernible in FIGS. 4 and 7. In this way, it is possible, for example during remagazination, to achieve transfer of the liquid sample to the test field area 136 of the particular analytical aid 112.

As explained above, according to the invention, the test element 122 is connected to the housing part 114 during a shaping process and, preferably, even by said shaping process. In the case of the analytical magazine 110 according to the exemplary embodiment shown, this is preferably achieved simultaneously for all the analytical aids 112 of the analytical magazine 110. However, other embodiments are also conceivable in principle. For this purpose, it is possible, for example, as in the exemplary embodiment shown, to use a support element 130 in the form of a circular-ring-shaped support film 132. Said support film 132 is coated with the test chemistry 134. The support element 130 is inserted into a shaping mold, for example an injection mold, by means of which the lower part 116 and thus the housing parts 114 are obtainable. The shaping mold is shaped such that the test chemistry 134 in the region of the subsequent test field areas 136 rests on a mold wall of the shaping mold, and so, in the shaping process, the test field areas 136 are not covered by housing material 158 of the housing part 114 or of the lower part 116. By contrast, in other regions in which no test field area 136 is to be subsequently produced, the test chemistry 134 is spaced from the wall of the shaping mold, and so these regions are embedded in the housing material 158. This is, for example, discernible in FIG. 5, which shows a cross-section through a wall section of the lower part 116 between two chambers 138. In this region, the test chemistry 134 is also embedded in the housing material 158.

After said insertion of the support element 130, coated with the test chemistry 134 and in the form of a test chemistry ring, into the shaping mold, the housing material 158 is introduced into said shaping mold, for example by injection or pressing, with the housing material 158 being in a liquid or at least deformable state. In this process step and/or a subsequent solidification step, with said steps being preferably carried out in the mold, the housing part 114 is connected directly to the support element 130 at at least one surface area 160. This can, for example, be promoted by the support element 130 and the housing material 158 being chemically similar, for example by using polycarbonates and/or polyesters.

The test chemistry ring, which provides support elements 130 and test chemistry 134 for the analytical aids 112, is therefore preferably subjected to in-mold coating (for example, in the region shown in FIG. 4) and/or overmolding (for example, in the region shown in FIG. 5) in said shaping process. In the region of the test field areas 136 in which the test chemistry 134 preferably rests on a mold wall of the shaping mold, it is possible to set temperatures during the shaping process which do not exceed, for example, 120° C. By suitable selection of the test chemistry 134, which withstands, at least for a short time, said temperatures, such a temperature rise is still acceptable. The observation window 146 can, for example, be made smaller in dimension than the test field area 136, and so, for example, edge regions of the test field areas 136 at which the test chemistry 134 comes into contact with the hot housing material 158 during the shaping process are not considered in the optical analysis. For example, the observation window 146 can, in each dimension, be made smaller in dimension than the test field area 136 by at least 5%, more particularly by at least 10% and, for example, by at least 30%, for example 30 to 50% smaller.

The described shaping process makes it possible, in a manner which is simple, reliable, and easily realizable on an industrial scale, to connect the test elements 122 of the analytical aids 112, preferably of all the analytical aids 112, to the housing parts 114 without, for example, the need for separate application of adhesive to the housing parts 114 and/or the test elements 112, in order to establish the connection between said elements. Thus, process steps can be saved. At the same time, as described above, the described aspect makes it possible to produce analytical aids 112 and analytical magazines 110 having low manufacturing tolerances, since manufacturing tolerances of an adhesive can, for example, be avoided.

Figure 8:
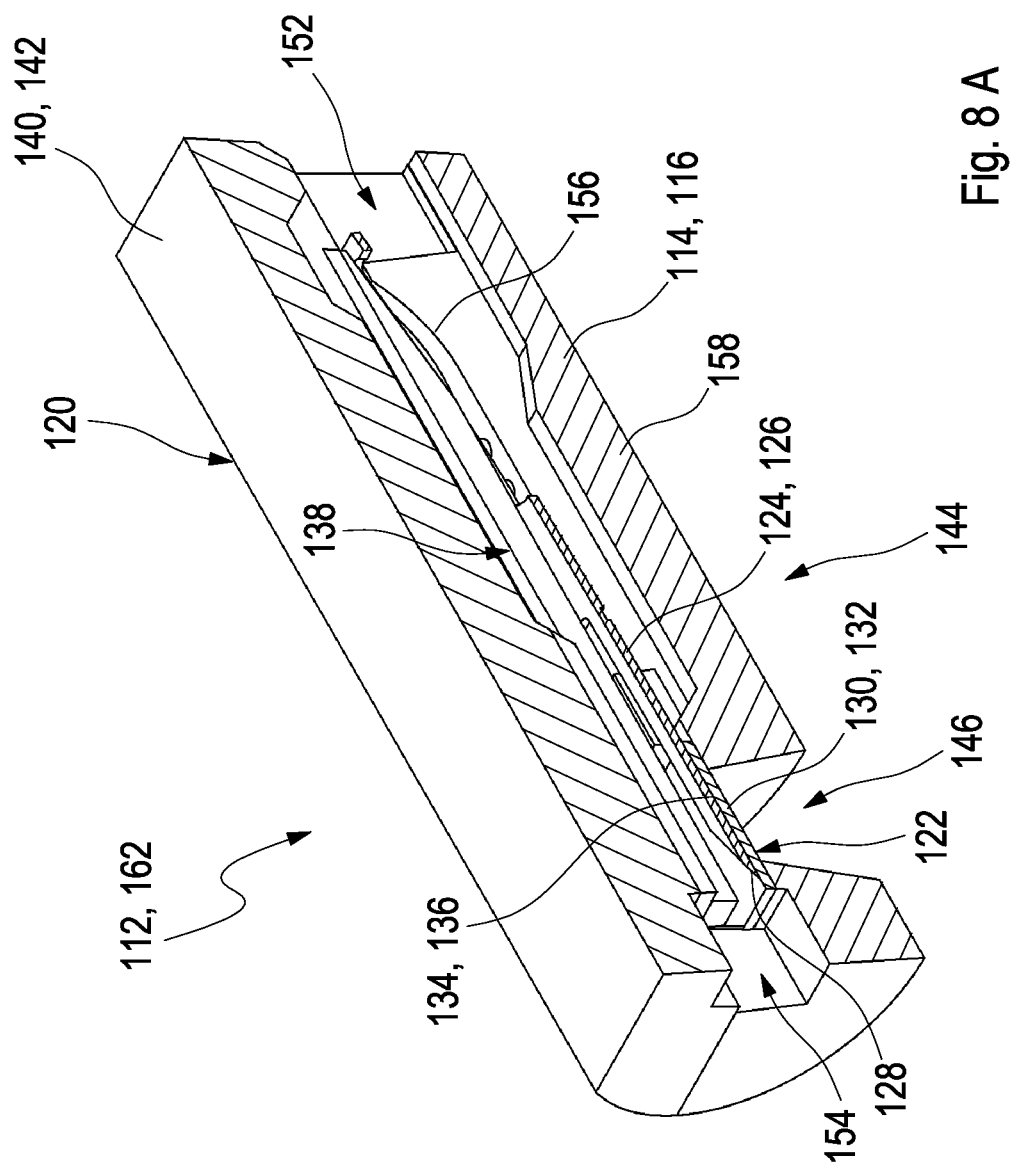
FIGS. 8A to 8G show various views of an exemplary embodiment of an analytical aid in the form of a single test.

FIGS. 8A-8G show various views of an analytical aid 112 in the form of an individual test 162. FIG. 8A shows a cross-sectional view through the individual test 162 along one axis of a chamber 138 of the individual test 162, FIG. 8B shows a front view of the individual test 162 looking towards a distal opening 154 for the exit of a lancet tip 128 of a lancet element 124, FIG. 8C shows a side view of the individual test 162, FIG. 8D shows a view of the individual test 162 looking from above with respect to FIG. 8C, FIG. 8E shows a cross-sectional view along the intersecting line A-A in FIG. 8D, FIG. 8F shows a view of the individual test 162 looking from below with respect to FIG. 8C, and FIG. 8D shows a perspective view of the individual test 162. The figures are explained together below.

As shown in FIG. 8A, the individual test 162 again comprises a housing 120 which is in the form of multiple parts. As is discernible in FIG. 8A, said housing 120 can, for example, comprise a housing part 114 in the form of a lower part 116 and a further housing part 140 as upper part 142. The housing 120 can enclose a chamber 138 in which optionally at least one lancet element 124 can be accommodated. Said lancet element 124 can, for example, be stored in a curved manner by means of corresponding contours 156, so that, as in the preceding exemplary embodiments, the lancet element 124 can be retained in the chamber 138 by its own spring tension. In this way, it is for example possible, even after a piercing operation, as explained above, to ensure reliable remagazination of the lancet element 124 in the chamber 138. The lancet element 124 can, for example, again be a microsampler 126.

The chamber 138 can, for example, have at least one exit opening for a lancet tip 128 of the lancet 124. Said exit opening is referred to here as distal opening 154. Optionally, the chamber 138 can have in addition at least one actuator opening or proximal opening 152. In this regard, reference can be made again to the above description of the analytical magazine.

In addition, the analytical aid again comprises a test element 122 comprising optionally a support element 130 and a test chemistry 134 which faces the interior space of the chamber 138 and which forms a test field area 136 on the side facing the chamber 138. In this regard, reference can, for example, be made to the description of FIG. 4 above.

The individual test 162 can in principle be produced analogously to the above-described production process. For this purpose, the finished test element 162 can, for example, be inserted into an appropriate mold, so that, for example, the test field area 136 completely or partly rests on one wall of the mold. Subsequently, a housing material which forms the housing part 114 can be introduced into the mold, for example injected, so that, as a result of the shaping process, the support element 130 is connected to the housing material and, at the same time, the housing part 114 is formed. For example, the support element 130 can be connected to the housing part 114 in a cohesive manner and without interposition of further connecting elements or connecting materials. In this regard, by way of example, reference can be made again to the above description of the analytical magazine 110.

The individual test 162 can, for example, additionally again comprise an observation window 146 on a detection side 144. By means of said observation window 146, it is for example possible, analogously to the above-described exemplary embodiments, to detect a change in at least one optical property of the test element 122 or the test chemistry 134 in a reaction with the sample and/or an analyte present in the sample.

The support element can, for example, again be in the form of a support film 132. With regard to possible materials, reference can be made to the above description. For example, polycarbonates and/or other plastics materials can be used, preferably transparent materials. As can, for example, be seen from the cross-sectional view in FIG. 8E, the test chemistry 134 outside of the test field area 136 which is accessible from the chamber 138 can be embedded in the housing material 158 of the housing part 114. The support element 130 can therefore preferably be coated with the test chemistry 134 prior to the shaping process, so that the test chemistry 134 is partly embedded in the housing material 158. For further details, reference can be made to the above description.

The individual test 162 can be handled individually, for example by said individual test 162 being individually acted on and used by an actuator (not shown). For example, the individual test 162 can optionally be stored on its own or can optionally be stored in a magazine with a plurality of other individual tests 162 and removed individually from the magazine for individual use. In the exemplary embodiment shown, the individual test 162 is therefore not directly mechanically connected to other individual tests 162, but can be used and handled as an individual element. For example, by means of an appropriate actuator system, it is possible for the individual test 162, independently of other individual tests, to be fed to an analytical test device and/or to be brought to an application position within the analytical test device in order to be used there. In said application position, a corresponding actuator can, for example, intrude into the chamber 138 through the proximal opening 152, grasp the lancet element 124 at one end facing the proximal opening 152, carry out a piercing movement comprising the lancet tip 128 briefly emerging through the distal opening 154 and pricking a skin surface. Blood and/or other body fluid are collected, and the lancet tip 128 is drawn back into the chamber 138. By means of the contours 156 and/or a separate actuator, the lancet tip 128 is guided past the test field area 136 in close proximity such that collected sample is transferred to the test field area 136 inside the chamber 138.

The housing 120 of the individual test 162 can comprise one or more housing contours and/or securing structures which can facilitate handling of the individual test 162 by means of a corresponding actuator. For example, one or more notches 164 can be provided at one side wall of the housing 120, which are discernible, for example, in FIGS. 8C, 8D, 8F and 8G. As an alternative or in addition to the notches 164, the individual test 162 can also optionally comprise one or more securing structures designed in a different way, so that in general the individual test 162 can preferably comprise one or more such securing structures which permit and/or facilitate interaction with an actuator system for the mechanical handling of the individual test 162.

Alternatively or in addition, other types of connecting elements can also be provided as securing structure. In addition, the perspective view in FIG. 8G also shows symbolically a piercing direction 166, i.e. a direction in which the lancet tip 128 discernible in FIG. 8A emerges from the distal opening 154 in order to penetrate an area of skin of a user, in order to be brought back, subsequently, into the chamber 138 contrary to the piercing direction 166.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

REFERENCE SYMBOLS LIST 110 analytical magazine
112 analytical aid
114 housing part
116 lower part
118 magazine housing
120 housing
122 test element
124 lancet element
126 microsampler
128 lancet tip
130 support element
132 support film
134 test chemistry
136 test field area
138 chamber
140 further housing part
142 upper part
144 detection side
146 observation window
148 transport element
150 central recess
152 proximal opening, actuator opening
154 distal opening
156 contours
158 housing material 160 surface area
162 individual test
164 groove
166 piercing direction

The invention claimed is:

1. A process for producing an analytical aid for the detection of at least one analyte in a sample, wherein the analytical aid comprises at least one housing and at least one test element comprising at least one test chemistry, wherein the process comprises the following steps:
   a) providing the test element comprising the test chemistry; and
   b) producing at least one housing part of the housing by means of at least one shaping process, during which the test element comprising the test chemistry is connected to the housing part,
   wherein, in step b), the test element is connected to the housing part such that at least one surface of the test chemistry as test field area for application of the sample remains uncovered by a housing material of the housing part, wherein the housing is configured such that at least one observation window is produced in the housing, wherein the test field area is optically monitorable through the observation window of the housing, wherein the process is carried out such that the housing forms at least one chamber, wherein the test field area faces an interior space of the chamber.

2. The process according to claim 1, wherein the shaping process comprises at least one casting process.

3. The process according to claim 1, wherein the shaping process comprises at least one plastics shaping process, wherein the plastics shaping process is selected from a back injection molding and an insert molding.

4. The process according to claim 1, wherein, in step b), at least part of the test element is inserted into a shaping mold and is at least partly contacted, in the shaping mold, with at least one housing material of the housing part, wherein the at least one part of the test element inserted into the shaping mold rests, via at least one section, on at least one wall of the shaping mold, wherein step b) is carried out such that the wall of the shaping mold, at least in the region on which the section of the test element rests on the wall, has a temperature of not more than 130° C. while step b) is being carried out.

5. The process according to claim 4, wherein the section of the test element which rests on the wall comprises at least part of the test chemistry.

6. The process according to claim 5, wherein the section of the test element which rests on the wall comprises a test field area of the test chemistry.

7. The process according to claim 4, wherein step b) is carried out such that the wall of the shaping mold, at least in the region on which the section of the test element rests on the wall, has a temperature of not more than 120° C. while step b) is being carried out.

8. The process according to claim 4, wherein step b) is carried out such that the wall of the shaping mold, at least in the region on which the section of the test element rests on the wall, has a temperature of not more than 110° C. while step b) is being carried out.

9. The process according to claim 1, wherein the test chemistry is selected in terms of stability such that it is stable, at least for a short time, with respect to temperatures of 100° C.

10. The process according to claim 9, wherein the test chemistry is selected in terms of stability such that it is stable, at least for a short time, with respect to temperatures of 110° C.

11. The process according to claim 9, wherein the test chemistry is selected in terms of stability such that it is stable, at least for a short time, with respect to temperatures of 120° C.

12. The process according to claim 1, wherein the test element comprises at least one support element, wherein the test chemistry is connected to the support element.

13. The process according to claim 12, wherein the support element is a disc-shaped support element, wherein the test chemistry is applied to the support element as a coating, and wherein the coating provides test field areas for the analytical aids.

14. The process according to claim 13, wherein the support element is a circular-disc-shaped support element.

15. The process according to claim 13, wherein the support element is a circular-ring-shaped support element.

16. The process according to claim 12, wherein the test chemistry is connected to the support element by applying at least one layer of the test chemistry to the support element.

17. The process according to claim 1, wherein a plurality of analytical aids is produced, wherein the process is carried out such that the analytical aids are contained in an analytical magazine.

18. The process according to claim 17, wherein the analytical aids are accommodated in a common magazine housing, wherein the process is carried out such that the housings of the analytical aids are constituents of the magazine housing.

19. The process according to claim 1, wherein the sample is a body fluid.

20. An analytical aid for the detection of at least one analyte in a sample, obtainable by a process according to claim 1, wherein the analytical aid comprises at least one housing comprising at least one housing part and at least one test element comprising at least one test chemistry, wherein the test element is connected to the housing part by means of a shaping process of the housing part, wherein, during the production of the housing part, the test element comprising the test chemistry is connected to the housing part such that at least one surface of the test chemistry as test field area for application of the sample remains uncovered by a housing material of the housing part, wherein the housing is configured such that at least one observation window is produced in the housing, wherein the test field area is optically monitorable through the observation window of the housing, wherein the housing forms at least one chamber, and wherein the test field area faces an interior space of the chamber.

21. The analytical aid according to claim 20, wherein the analytical aid comprises at least one lancet element for generating the sample.

22. The analytical aid according to claim 21, wherein the at least one lancet element is at least one microsampler.

23. The analytical aid according to claim 20, wherein the housing comprises at least one observation window accessible from an outer side of the housing, wherein at least one property change of the test element, is detectable from outside through the observation window.

24. The analytical aid according to claim 23, wherein the observation window is configured such that at least one test field area of the test element is observable through at least one support element, which is at least partially optically transparent, of the test element.

25. The analytical aid according to claim 23, wherein the at least one property change of the test element is selected from the group consisting of at least one color change and at least one change in at least one optical property.

26. An analytical magazine comprising a plurality of the analytical aids of claim 20.

\* \* \* \* \*